(12) United States Patent
Phan et al.

(10) Patent No.: US 6,706,698 B2
(45) Date of Patent: *Mar. 16, 2004

(54) α-SUBSTITUTED β-AMINOETHYL PHOSPHONATE DERIVATIVES

(75) Inventors: Hieu Trung Phan, Tannay (CH); Lan Mong Nguyen, Nyon (CH); Vinh Van Diep, Vetraz-Monthoux (FR); Raymond Azoulay, Geneva (CH); Harald Eschenhof, Geneva (CH); Eric Joseph Niesor, Nyon (CH); Craig Leigh Bentzen, Bogis-Bossey (CH); Robert John Ife, Stevenage (GB)

(73) Assignee: Ilex Products, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/963,900

(22) Filed: Sep. 26, 2001

(65) Prior Publication Data

US 2002/0111332 A1 Aug. 15, 2002

(30) Foreign Application Priority Data

Sep. 27, 2000 (GB) .............................. 0023705
Oct. 20, 2000 (GB) .............................. 0025783

(51) Int. Cl.$^7$ ...................... A01N 57/00; A61K 31/675; C07F 9/02; C07F 9/06
(52) U.S. Cl. ........................... 514/79; 514/80; 514/85; 514/86; 514/89; 514/91; 514/92; 514/96; 544/232; 544/243; 544/337; 546/22; 546/26; 548/112; 548/113
(58) Field of Search ............. 514/79, 80, 85, 514/86, 89, 91, 92, 96; 544/232, 243, 337; 546/22, 26; 548/112, 113

(56) References Cited

U.S. PATENT DOCUMENTS

| | | | |
|---|---|---|---|
| 5,424,303 A | 6/1995 | Phan et al. | 514/89 |
| 5,441,946 A | 8/1995 | Pauls et al. | 514/114 |
| 6,060,464 A | 5/2000 | Nguyen et al. | 514/89 |
| 6,117,873 A | 9/2000 | Acklin et al. | 514/249 |
| 6,303,784 B1 | 10/2001 | Nguyen et al. | 546/24 |

FOREIGN PATENT DOCUMENTS

| | | | |
|---|---|---|---|
| CA | 2158517 | 9/1995 | C07F/9/38 |
| JP | 07059765 | 2/1995 | C07F/9/553 |
| WO | PCT/GB97/03479 | 12/1997 | C07F/9/58 |
| WO | PCT/EP97/07192 | 12/1997 | C07F/9/58 |

OTHER PUBLICATIONS

Siepak et al, Pharmazie vol. 36(11), pp. 782–783 (1981)—As abstracted by Chem. Abstracts (CAPLUS).*

Karimov et al., Necleophilic Addition of Amines to Dialkyl 1–Phenylethenyl–Phosphonate, J. Gen Chem. USSR 59:904–905, 1989.

Ing, "The Pharmacology of Homolous Series," pp. 306–309, In: Progress in Drug Research, Ed. Jucker, Birkhaeuser Verlag, VOL 7. 1964.

Siepak et al.; "Investigation on antibacterial activity of some new aminophosphinic and aminophosphonic complexons," *Pharmazie*, 36:782–783, 1981.

Co–pending U.S. application No. 10/012,785, by H. T. Phan et al., filed Oct. 22, 2001.

* cited by examiner

*Primary Examiner*—Mukund J. Shah
*Assistant Examiner*—Zachary C. Tucker
(74) *Attorney, Agent, or Firm*—Fulbright & Jaworski L.L.P

(57) ABSTRACT

The present invention relates to novel α-substituted-β-aminoethylphosphonate and α-substituted-β-aminovinylphosphonate derivatives and their uses for lowering plasma levels of apo (a), Lp(a), apo B, apo B associated lipoproteins (low density lipoproteins and very low density lipoproteins) and for lowering plasma levels of total cholesterol.

18 Claims, No Drawings

α-SUBSTITUTED β-AMINOETHYL PHOSPHONATE DERIVATIVES

FIELD OF THE INVENTION

This invention relates to substituted aminoethylphosphonate compositions and therapeutic uses thereof. More specifically, the present invention relates to novel α-substituted-β-aminoethylphosphonate and α-substituted-β-aminovinylphosphonate derivatives, processes for their preparations, pharmaceutical compositions containing them and their use in therapy, for lowering plasma levels of apo (a) and apo (a) associated lipoprotein (lipoprotein(a) or "Lp(a)"), for lowering plasma levels of apo B and apo B associated lipoproteins (low density lipoproteins and very low density lipoproteins), and for lowering plasma levels of total cholesterol.

BACKGROUND OF THE INVENTION

Lp(a) is a LDL-like lipoprotein wherein the major lipoprotein, apo B-100, is covalently linked to an unusual glycoprotein, apoprotein(a). The covalent association between apo(a) and apo B to form Lp(a) is a secondary event which is independent of the plasma concentration of apo B. Due to its structural similarity to plasminogen, apo(a) interferes with the normal physiological thrombosis-hemostasis process by preventing thrombolysis, that is clot dissolution (see e.g., Biemond B J, Circulation 1997, 96(5) 1612–1615). The structural feature of Lp(a), where the LDL lipoprotein is linked to apo(a), is thought to be responsible for its atherogenic and thrombogenic activities.

Elevated levels of Lp(a) have been associated with the development of atherosclerosis, coronary heart disease, myocardial infarction, cerebral infarction, restenosis following balloon angioplasty and stroke. A recent epidemiologic study has provided the clinical proof of a positive correlation between plasma Lp(a) concentrations and the incidence of heart disease (A. G. Bostom, et al., Journal of American Medical Association 1996, 276, p. 544–548).

Patients that have Lp(a) levels in excess of 20–30 mg/dl run a significantly increased risk of heart attacks and stroke. An effective therapy for lowering Lp(a) does not exist at present because cholesterol lowering agents such as the HMGCoA reductase inhibitors do not lower Lp(a) plasma concentrations. The only compound that lowers Lp(a) is niacin, but the high doses necessary for activity are accompanied with unacceptable side-effects. There is, therefore, an unmet therapeutic need for agents that effectively reduce elevated levels of Lp(a).

International applications WO 97/20307, WO 98/28310, WO 98/28311 and WO 98/28312 (Symphar, SmithKline Beecham) describe a series of α-amino phosphonates which have Lp(a) lowering activity. There however remains the need to identify further compounds having Lp(a) lowering activity.

SUMMARY OF THE INVENTION

The present invention provides, in a first aspect, a compound of formula (Ia):

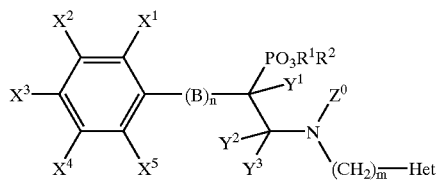

or a compound of formula (Ib):

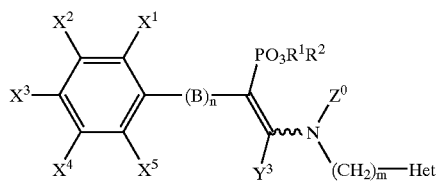

in which:
$X^1, X^2, X^3, X^4$ and $X^5$ are independently hydrogen, hydroxy, hydroxymethyl, $C_1$–$C_3$ alkoxymethyl, straight or branched $C_1$–$C_8$ alkyl, straight or branched $C_1$–$C_8$ alkoxy, $C_3$–$C_6$ cycloalkyl, $C_3$–$C_6$ cycloalkoxy, norbornyl, adamantyl, amino, primary or secondary amino substituted with $C_1$–$C_3$ alkyl, cyano, halogen (F, Cl, Br, I), and nitro; or $X^2$ may be combined with $X^3$, or $X^4$ may be combined with $X^5$, to form a 5- to 6-membered alkylidenedioxy ring optionally substituted with a $C_1$–$C_4$ alkyl group; or $X^4$ may be combined with $X^5$ to form a 5- to 6-membered alkylidene ring optionally substituted with a $C_1$–$C_4$ alkyl group;

$R^1$ and $R^2$ which may be the same or different, are independently hydrogen or a straight or branched $C_1$–$C_6$ alkyl;

B is $CH_2$ or $CH_2$—$CH_2$;

n is zero or 1;

$Z^0$ is H, straight or branched $C_1$–$C_4$ alkyl, $C_1$–$C_4$ alkylcarbonyl, or $C_1$–$C_4$ perfluoroalkylcarbonyl;

m is zero or an integer from 1 to 4;

Het is an optionally substituted heteroaryl group comprising at least one nitrogen atom, or a pharmaceutically acceptable salt thereof;

for a compound of formula (Ia), $Y^1$, $Y^2$ and $Y^3$ are independently hydrogen or $C_1$–$C_4$ alkyl and for a compound of formula (Ib), $Y^3$ is hydrogen or $C_1$–$C_4$ alkyl.

The compound of formula (Ib) may be the Z-isomer, the E-isomer, or a mixture thereof.

Compounds of the present invention include:
(Z)-diethyl α-(3,5-dimethoxy-4-hydroxyphenyl)-β-[N-(3-pyridyl)-amino]-vinylphosphonate;
(Z)-diethyl α-(4-hydroxy-3-methoxy-5-methylphenyl)-β-[N-(3-pyridyl)-amino]-vinylphosphonate;
(Z)-diisopropyl α-(4-hydroxy-3-methoxy-5-methylphenyl)-β-[N-(3-pyridyl)-amino]-vinylphosphonate;
(E)-diethyl α-(3,5-dimethoxy-4-hydroxyphenyl)-β-[N-(3-pyridyl)-amino]-vinylphosphonate;
(E)-diisopropyl α-(3,5-dimethoxy-4-hydroxyphenyl)-β-[N-(3-pyridyl)-amino]-vinylphosphonate;
(E)-Diethyl α-(4-hydroxy-3-methoxy-5-methylphenyl)-β-[N-(3-pyridyl)-amino]-vinylphosphonate;
(E)-diisopropyl α-(4-hydroxy-3-methoxy-5-methylphenyl)-β-[N-(3-pyridyl)-amino]-vinylphosphonate;
diethyl α-(3,5-dimethoxy-4-hydroxyphenyl)-β-[N-(3-pyridyl)-amino]-ethylphosphonate;
diisopropyl α-(3,5-dimethoxy-4-hydroxyphenyl)-β-[N-(3-pyridyl)-amino]-ethylphosphonate;

diethyl α-(4-hydroxy-3-methoxy-5-methylphenyl)-β-[N-(3-pyridyl)-amino]-ethylphosphonate;
diisopropyl α-(4-hydroxy-3-methoxy-5-methylphenyl)-β-[N-(3-pyridyl) amino]-ethylphosphonate;
(Z)-diethyl α-(3,5-dimethoxy-4-hydroxyphenyl)-β-[N-(3-(2,6-dimethyl)pyridyl))-amino]-vinylphosphonate;
(Z)-diethyl α-(4-hydroxy-3-methoxy-5-methylphenyl)-β-[N-(3-(2,6-dimethyl)pyridyl))-amino]-vinylphosphonate;
(E)-diisopropyl α-(3,5-dimethoxy-4-hydroxyphenyl)-β-[N-(3-(2,6-dimethyl)pyridyl))-amino]-vinylphosphonate;
(E)-diethyl α-(4-hydroxy-3-methoxy-5-methylphenyl)-β-[N-(3-(2,6-dimethyl)pyridyl))-amino]-vinylphosphonate;
(E)-diisopropyl α-(4-hydroxy-3-methoxy-5-methylphenyl)-β-[N-(3-(2,6-dimethyl)pyridyl))-amino]-vinylphosphonate;
diethyl α-(3,5-dimethoxy-4-hydroxyphenyl)-β-[N-(3-(2,6-dimethyl)pyridyl))-amino]-ethylphosphonate;
diisopropyl α-(3,5-dimethoxy-4-hydroxyphenyl)-β-[N-(3-(2,6-dimethyl)pyridyl))-amino]-ethylphosphonate;
diisopropyl α-(4-hydroxy-3-methoxy-5-methylphenyl)-β-[N-(3-(2,6-dimethyl)pyridyl))-amino]-ethylphosphonate;
(E)-diethyl α-(4-hydroxy-3-methoxy-5-methylphenyl)-β-[N-(5-(2-methyl)pyridyl))-amino]-vinylphosphonate;
diethyl α-(4-hydroxy-3-methoxy-5-methylphenyl)-β-[N-(5-(2-methyl)pyridyl))-amino]-ethylphosphonate;
(E)-diethyl α-(4-hydroxy-3-methoxy-5-methylphenyl)-β-[N-(5-(2-methoxy)pyridyl))-amino]-vinylphosphonate;
diethyl α-(4-hydroxy-3-methoxy-5-methylphenyl)-β-[N-(5-(2-methoxy)pyridyl))-amino]-ethylphosphonate;
(Z)-diethyl α-(3,5-dimethoxy-4-hydroxyphenyl)-β-[N-(pyrazinyl)-amino]-vinylphosphonate;
(Z)-diisopropyl α-(3,5-dimethoxy-4-hydroxyphenyl)-β-[N-(pyrazinyl)-amino]-vinylphosphonate;
(Z)-diethyl α-(4-hydroxy-3-methoxy-5-methylphenyl)-β-[N-(pyrazinyl)-amino]-vinylphosphonate;
(E)-diisopropyl α-(3,5-dimethoxy-4-hydroxyphenyl)-β-[N-(pyrazinyl)-amino]-vinylphosphonate;
(E)-diethyl α-(4-hydroxy-3-methoxy-5-methylphenyl)-β-[N-(pyrazinyl)-amino]-vinylphosphonate;
diethyl α-(3,5-dimethoxy-4-hydroxyphenyl)-β-[N-(pyrazinyl)-amino]-ethylphosphonate;
diisopropyl α-(3,5-dimethoxy-4-hydroxyphenyl)-β-[N-(pyrazinyl)-amino]-ethylphosphonate;
diethyl α-(4-hydroxy-3-methoxy-5-methylphenyl)-β-[N-(pyrazinyl)-amino]-ethylphosphonate;
(Z)-diethyl α-(3,5-dimethoxy-4-hydroxyphenyl)-β-[N-(2-pyrimidinyl)-amino]-vinylphosphonate;
(Z)-diisopropyl α-(3,5-dimethoxy-4-hydroxyphenyl)-β-[N-(2-pyrimidinyl)-amino]-vinylphosphonate;
(E)-diethyl α-(3,5-dimethoxy-4-hydroxyphenyl)-β-[N-(2-pyrimidinyl)-amino]-vinylphosphonate;
(E)-diisopropyl α-(3,5-dimethoxy-4-hydroxyphenyl)-β-[N-(2-pyrimidinyl)-amino]-vinylphosphonate;
diisopropyl α-(3,5-dimethoxy-4-hydroxyphenyl)-β-[N-(2-pyrimidinyl)-amino]-ethylphosphonate;
(Z)-diethyl α-(4-hydroxy-3-methoxy-5-methylphenyl)-β-[N-(2-pyrimidinyl)-amino]-vinylphosphonate;
(Z)-diisopropyl α-(3,5-dimethyl-4-hydroxyphenyl)-β-[N-(3-(2,6-dimethylpyridyl))-amino]-vinylphosphonate;
(E)-diethyl α-(4-hydroxy-3-methoxy-5-methylphenyl)-β-[N-(2-pyrimidinyl)-amino]-vinylphosphonate;
(E)-diethyl α-(3,5-dimethyl-4-hydroxyphenyl)-β-[N-(3-pyridyl)-amino]-vinylphosphonate;
(E)-diisopropyl α-(3,5-dimethyl-4-hydroxyphenyl)-β-[N-(3-pyridyl)-amino]-vinylphosphonate;
(E)-diethyl α-(3,5-dimethyl-4-hydroxyphenyl)-β-[N-(3-(2,6-dimethylpyridyl))-amino]-vinylphosphonate;
(E)-diethyl α-(3,5-dimethyl-4-hydroxyphenyl)-β-[N-(5-(2-methylpyridyl))-amino]-vinylphosphonate;
(E)-diisopropyl α-(3,5-dimethyl-4-hydroxyphenyl)-β-[N-(5-(2-methylpyridyl))-amino]-vinylphosphonate;
diethyl α-(3,5-dimethyl-4-hydroxyphenyl)-β-[N-(3-pyridyl)-amino]-ethylphosphonate;
diisopropyl α-(3,5-dimethyl-4-hydroxyphenyl)-β-[N-(3-pyridyl)-amino]-ethylphosphonate;
diethyl α-(3,5-dimethyl-4-hydroxyphenyl)-β-[N-(3-(2,6-dimethylpyridyl))-amino]-ethylphosphonate;
diisopropyl α-(3,5-dimethyl-4-hydroxyphenyl)-β-[N-(3-(2,6-dimethylpyridyl))-amino]-ethylphosphonate;
diethyl α-(3,5-dimethyl-4-hydroxyphenyl)-β-[N-(5-(2-methylpyridyl))-amino]-ethylphosphonate;
diisopropyl α-(3,5-dimethyl-4-hydroxyphenyl)-β-[N-(5-(2-methylpyridyl))-amino]-ethylphosphonate;
(E)-diisopropyl α-(3,5-dimethyl-4-hydroxyphenyl)-β-[N-(3-(2,6-dimethylpyridyl))-amino]-vinylphosphonate;
diethyl α-(4-hydroxy-3-methoxy-5-methylphenyl)-β-[N-(2-pyrimidinyl)-amino]-ethylphosphonate;
(E)-diethyl α-(3-ethoxy-4-hydroxy-5-methylphenyl)-β-[N-(3-pyridyl)-amino]-vinylphosphonate;
diethyl α-(3-ethoxy-4-hydroxy-5-methylphenyl)-β-[N-(3-pyridyl)-amino]-ethylphosphonate;
(E)-diethyl α-(3-ethoxy-4-hydroxy-5-methylphenyl)-β-[N-(3-(2,6-dimethylpyridyl))-amino]-vinylphosphonate;
diethyl α-(3-ethoxy-4-hydroxy-5-methylphenyl)-β-[N-(3-(2,6-dimethylpyridyl))-amino]-ethylphosphonate;
(E)-diisopropyl α-(3-ethoxy-4-hydroxy-5-methylphenyl)-β-[N-(3-(2,6-dimethylpyridyl))-amino]-vinylphosphonate;
diisopropyl α-(3-ethoxy-4-hydroxy-5-methylphenyl)-β-[N-(3-(2,6-dimethylpyridyl))-amino]-ethylphosphonate;
diethyl α-(4-hydroxy-3-methoxy-5-methylphenyl)-β-[N-(2-(4,6-dimethyl)pyridyl))-amino]-ethylphosphonate;
diethyl α-(4-hydroxy-3-methoxy-5-methylphenyl)-β-[N-(2-(4,6-dimethylpyrimidinyl))-amino]-ethylphosphonate;
diethyl α-(4-hydroxy-3-methoxy-5-methylphenyl)-β-[N-(2-(4-methoxy-6-methylpyrimidinyl))-amino]-ethylphosphonate;
(E)-diethyl α-(4-hydroxy-3-methoxy-5-methylphenyl)-β-[N-(5-pyrimidinyl)-amino]-vinylphosphonate;
diethyl α-(4-hydroxy-3-methoxy-5-methylphenyl)-β-[N-(5-pyrimidinyl)-amino]-ethylphosphonate;
diethyl α-(4-hydroxy-3-methoxy-5-methylphenyl)-β-[N-(5-(2-methylpyrimidinyl)-amino]-ethylphosphonate;
(Z)-diethyl α-(4-hydroxy-3-methoxy-5-methylphenyl)-β-[N-(5-(4-methylpyrimidinyl))-amino]-vinylphosphonate;
(E)-diethyl α-(4-hydroxy-3-methoxy-5-methylphenyl)-β-[N-(5-(4-methylpyrimidinyl))-amino]-vinylphosphonate;
diethyl α-(4-hydroxy-3-methoxy-5-methylphenyl)-β-[N-(5-(4-methylpyrimidinyl))-amino]-ethylphosphonate;
(Z)-diethyl α-(4-hydroxy-3-methoxy-5-methylphenyl)-β-[N-(5-(2,6-dimethylpyrimidinyl))-amino]-vinylphosphonate;
(E)-diethyl α-(4-hydroxy-3-methoxy-5-methylphenyl)-β-[N-(5-(2,6-dimethylpyrimidinyl))-amino]-vinylphosphonate;
diethyl α-(4-hydroxy-3-methoxy-5-methylphenyl)-β-[N-(5-(2,6-dimethylpyrimidinyl))-amino]-ethylphosphonate;
diethyl α-(4-hydroxy-3-methoxy-5-methylphenyl)-β-[N-(2-thiazolyl)-amino]-ethylphosphonate;
diethyl α-(4-hydroxy-3-methoxy-5-methylphenyl)-β-[N-(2-(5-methylthiazolyl))-amino]-ethylphosphonate;
diethyl α-(4-hydroxy-3-methoxy-5-methylphenyl)-β-[N-(2-(1,3,4-thiadiazolyl)-amino]-ethylphosphonate;
diethyl α-(4-hydroxy-3-methoxy-5-methylphenyl)-β-[N-(2-(5-methyl-1,3,4-thiadiazolyl))-amino]-ethylphosphonate;

(E)-diethyl α-(4-hydroxy-3-methoxy-5-methylphenyl)-β-[N-(2-(5-methylpyrazinyl))-amino]-vinylphosphonate;
diethyl α-(4-hydroxy-3-methoxy-5-methylphenyl)-β-[N-(2-(5-methylpyrazinyl))-amino]-ethylphosphonate;
diethyl α-(4-hydroxy-3-methoxy-5-methylphenyl)-β-[N-(3-(6-methylpyridazinyl))-amino]-ethylphosphonate;
(E)-diethyl α-(4-hydroxy-3-methoxy-5-methylphenyl)-β-[N-(4-(1,3,5-trimethylpyrazolyl))-amino]-vinylphosphonate;
diethyl α-(4-hydroxy-3-methoxy-5-methylphenyl)-β-[N-(4-(1,3,5-trimethylpyrazolyl))-amino]-ethylphosphonate;
diethyl α-(4-hydroxy-3-methoxy-5-methylphenyl)-β-[N-(2-benzothiazolyl)-amino]-ethylphosphonate;
diethyl α-(4-hydroxy-3-methoxyphenyl)-β-[N-(3-(2,6-dimethyl)pyridyl))-amino]-ethylphosphonate;
diethyl α-(3-hydroxy-4-methoxyphenyl)-β-[N-(3-(2,6-dimethyl)pyridyl))-amino]-ethylphosphonate;
dimethyl α-(4-hydroxy-3-methoxy-5-methylphenyl)-β-[N-(3-pyridyl)-amino]-ethylphosphonate;
dimethyl α-(4-hydroxy-3-methoxy-5-methylphenyl)-β-[N-(3-(2,6-dimethylpyridyl))-amino]-ethylphosphonate;
diethyl α-(4-hydroxy-3-methoxy-5-methylphenyl)-β-[N-(5-(1,3-dimethylpyrazolyl))-amino]-ethylphosphonate;
diethyl α-(4-hydroxy-3-methoxy-5-methylphenyl)-β-[N-(3-isoxazolyl)-amino]-ethylphosphonate;
diethyl α-(4-hydroxy-3-methoxy-5-methylphenyl)-β-[N-(3-(5-methylisoxazolyl))-amino]-ethylphosphonate;
diethyl α-(4-hydroxy-3-methoxy-5-methylphenyl)-β-[N-(5-(3-methylisoxazolyl))-amino]-ethylphosphonate;
diethyl α-(4-hydroxy-3-methoxy-5-methylphenyl)-β-[N-(2-(4-methyloxazolyl))-amino]-ethylphosphonate;
diethyl α-(4-hydroxy-3-methoxy-5-methylphenyl)-β-[N-(2-(4-methylthiazolyl))-amino]-ethylphosphonate;
diethyl (α-phenyl-β-[N-(3-(2,6-dimethylpyridyl))-amino]-ethylphosphonate;
diethyl α-(4-chlorophenyl)-β-[N-(3-(2,6-dimethylpyridyl))-amino]-ethylphosphonate;
diethyl α-(4-methylphenyl)-β-[N-(3-(2,6-dimethylpyridyl))-amino]-ethylphosphonate;
diethyl α-(4-methoxyphenyl)-β-[N-(3-(2,6-dimethylpyridyl))-amino]-ethylphosphonate;
diethyl α-(4-hydroxy-3-methoxy-5-methylphenyl)-β-[N-methyl-N-(3-picolyl)-amino]-ethylphosphonate;
diethyl α-(4-hydroxy-3-methoxy-5-methylphenyl)-β-[N-methyl-N-(2-pyridyl)-amino]-ethylphosphonate;
diethyl α-(4-hydroxy-3-methoxy-5-methylphenyl)-β-[N-methyl-N-(2-(2-ethylpyridyl))-amino]-ethylphosphonate;
diethyl α-methyl-α-(4-hydroxy-3-methoxy-5-methylphenyl)-β-[N-(3-(2,6-dimethylpyridyl))-amino]-ethylphosphonate;
diethyl α-(3,5-dimethyl-4-hydroxyphenyl)-β-[N-(pyrazinyl)-amino]-ethylphosphonate;
diethyl α-(3-tert-butyl-4-hydroxy-5-methylphenyl)-β-[N-(pyrazinyl)-amino]-ethylphosphonate;
diethyl α-methyl-α-(4-hydroxy-3-methoxy-5-methylphenyl)-β-[N-pyrazinyl)-amino]-ethylphosphonate; and
diethyl α-(4-hydroxy-3-methoxy-5-methylphenyl)-β-[N-(3-(2,6-dimethyl)-aminopyridyl]-propylphosphonate.

Compounds of the present invention also include the following racemates and enantiomers:
(±)-diethyl α-(3,5-dimethoxy-4-hydroxyphenyl)-β-[N-(pyrazinyl)-amino]-ethylphosphonate;
(±)-diethyl α-(4-hydroxy-3-methoxy-5-methylphenyl)-β-[N-(pyrazinyl)-amino]-ethylphosphonate;
(±)-diisopropyl α-(4-hydroxy-3-methoxy-5-methylphenyl)-β-[N-3-(2,6-dimethyl)pyridyl-amino]-ethylphosphonate;
(±)-diethyl α-(4-hydroxy-3-methoxy-5-methylphenyl)-β-[N-(3-(2,6-dimethylpyridyl))-amino]-ethylphosphonate; and
(+) and (−)-diethyl α-(4-hydroxy-3-methoxy-5-methylphenyl)-β-[N-(3-(2,6-dimethylpyridyl))-amino]-ethylphosphonate, in particular the (+)-enantiomer, and pharmaceutically acceptable salts thereof, especially the dihydrogen phosphate salt.

One aspect of the present invention provides for a pharmaceutical composition comprising a compound of formula (Ia) or formula (Ib) and a pharmaceutically acceptable excipient. Hereinafter compounds of formula (Ia) and compounds of formula (Ib) are collectively termed "compounds of formula (I)."

The present invention also provides for therapeutic uses of the compounds of formula (I). In one aspect, the invention provides for a method of decreasing plasma levels of apo (a) and lipoprotein(a), in reducing plasma levels of apo B and LDL cholesterol and in decreasing plasma total cholesterol. The present invention also provides further methods including: a method of treatment of thrombosis by increasing thrombolysis through decreasing plasma levels of apo (a) and lipoprotein(a); a method of treatment of restenosis following angioplasty by decreasing plasma levels of apo (a) and lipoprotein(a); a method of prevention and/or treatment of atherosclerosis by decreasing plasma levels of apo (a) and lipoprotein(a) or by decreasing plasma levels of apoprotein B and LDL cholesterol; a method of prevention and/or treatment of hypercholesterolemia; a method of prevention and/or treament of atherosclerosis by lowering cholesterol in patients that are resistant to treatment with statins; and a method of prevention and/or treatment of atherosclerosis in association with a compound such as a statin which decreases cholesterol synthesis.

DETAILED DESCRIPTION OF THE INVENTION

The present invention relates to the compounds of formula (I) and their uses for lowering plasma levels of apo (a), Lp(a), apo B, apo B associated lipoproteins (low density lipoproteins and very low density lipoproteins) and for lowering plasma levels of total cholesterol.

In relation to compounds of formula (I), in preferred embodiments, $X^1$ is hydrogen, or methyl, $X^2$ is methoxy, ethoxy, methyl or hydroxy, $X^3$ is hydrogen, hydroxy, methoxy, methyl, ethyl or hydroxymethyl, $X^4$ is hydrogen, methoxy or methyl and $X^5$ is hydrogen. In a preferred combination, $X^2$ is methoxy, $X^3$ is hydroxy and $X^4$ is methyl or methoxy, preferably methyl. Preferably, n is zero, so that (B), is replaced with a direct bond. Preferably $R^1$ and $R^2$ are $C_1$–$C_3$ alkyl, more preferably $C_2$ or $C_3$, and in particular wherein $R^1$ and $R^2$ are independently ethyl or isopropyl. Preferably m is zero. Preferably, $Y^1$, $Y^2$ and $Y^3$ are independently selected from hydrogen or $C_1$–$C_4$ alkyl, more preferably $Y^2$ and $Y^3$ are each hydrogen for a compound of formula (Ia) and $Y^3$ is hydrogen for a compound of formula (Ib).

When used herein the term "heteroaryl" refers to, unless otherwise defined, a single or a fused ring containing up to four heteroatoms in each ring, each of which is selected from oxygen, nitrogen and sulphur, which rings, may be unsubstituted or substituted by, for example, up to four substituents. Each ring suitably has from 4 to 7, preferably 5 or 6 ring atoms. A fused ring system may include carbocyclic rings and need include only one heteroaryl ring.

Representative examples of Het include pyridyl, pyrimidyl, pyrazinyl, pyridazinyl, thiazolyl, thiadiazolyl, benzothiazolyl, isoxazolyl, pyrazolyl, triazinyl, and imidazolyl which may be unsubstituted or substituted by up to four substituents (for pyridyl and benzothiazolyl), three substituents (pyrimidyl, pyrazinyl, pyridazinyl, pyrazolyl), two substituents (thiazolyl, isoxazolyl, triazinyl and imidazolyl) or one substituent (thiadiazolyl) which may be the same or different and selected from straight or branched $C_1$–$C_4$ alkyl or alkoxy, hydroxy, hydroxymethyl, halogen (F, Cl, Br, I), or an amino group optionally substituted with $C_1$–$C_4$ alkyl. Preferably, pyridyl, pyrimidyl, pyrazinyl, pyridazinyl, thiazolyl, thiadiazolyl, benzothiazolyl, pyrazolyl, or triazinyl is unsubstituted or substituted by methyl, methoxy, dimethoxy or dimethyl. Preferred examples of Het are 2,6-dimethylpyridyl and pyrazinyl.

Pharmaceutically acceptable salts for use in the present invention include those described by Berge, Bighley, and Monkhouse, *J. Pharm. Sci.*, 1977, 66, 1–19. Such salts may be formed from inorganic and organic acids. Representative examples thereof include maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

It will be appreciated that certain compounds of the present invention, in particular those of formula (Ia), will comprise one or more chiral centres so that compounds may exist as stereoisomers, including diastereoisomers and enantiomers. The present invention covers all such stereoisomers, and mixtures thereof, including racemates. The compounds of formula (Ib) of the present invention comprise the individual E- and Z-diastereoisomers and mixtures thereof.

Since the compounds of the present invention, in particular compounds of formula (Ia) and (Ib) (collectively the compounds of formula (I)), are intended for use in pharmaceutical compositions, it will be understood that they are each provided in substantially pure form, for example at least 50% pure, more suitably at least 75% pure and preferably at least 95% pure (% are on a wt/wt basis). Impure preparations of the compounds of formula (I) may be used for preparing the more pure forms used in the pharmaceutical compositions. Although the purity of intermediate compounds of the present invention is less critical, it will be readily understood that the substantially pure form is preferred as for the compounds of formula (I). Preferably, whenever possible, the compounds of the present invention are obtained in crystalline form.

When some of the compounds of this invention are allowed to crystallise or are recrystallised from organic solvents, solvent of crystallisation may be present in the crystalline product. This invention includes within its scope such solvates. Similarly, some of the compounds of this invention may be crystallised or recrystallised from solvents containing water. In such cases water of hydration may be formed. This invention includes within its scope stoichiometric hydrates as well as compounds containing variable amounts of water that may be produced by processes such as lyophilisation. In addition, different crystallisation conditions may lead to the formation of different polymorphic forms of crystalline products. This invention includes within its scope all polymorphic forms of the compounds of formula (I).

The present invention also relates to the unexpected discovery that compounds of formula (I) are effective for decreasing apo(a) production in vitro and Lp(a) production in vivo in Cynomolgus monkeys. This species has been selected as the animal model as its Lp(a) is similar in immunologic properties to human Lp(a) and occurs in almost identical frequency distribution of plasma concentrations, see e.g., N. Azrolan et al; J. Biol. Chem., 266, 13866–13872 (1991). In the in vitro assay, compounds of formula (I) have been shown to reduce the secretion of apo (a) which is secreted in free form from the primary cultures of the Cynomolgus monkey hepatocytes. These results are confirmed by the in vivo studies performed on the same animal species showing the potent decrease of Lp(a) by compounds of formula (I). Therefore the compounds of this invention are useful for decreasing apo (a) and Lp(a) in man and thus provide a therapeutic benefit.

Accordingly in a further aspect, this invention provides a compound of formula (I) or a pharmaceutically acceptable salt thereof for use in therapy, in particular as a Lp(a) lowering agent. Elevated plasma and tissue levels of Lp(a) are associated with accelerated atherosclerosis, abnormal proliferation of smooth muscle cells and increased thrombogenesis and expressed in disease states such as, for instance: coronary heart disease, peripheral artery disease, intermittent claudication, thrombosis, restenosis after angioplasty, extra-cranial carotid atherosclerosis, stroke and atherosclerosis occurring after heart transplantion.

Furthermore, the compounds of the present invention have been found to have potent cholesterol lowering properties. Thus, studies performed in Cynomolgus monkeys have shown that the compounds of the present invention decrease total plasma cholesterol, in particular LDL cholesterol. It is now well established that a high level of LDL cholesterol is a major risk factor for atherosclerotic diseases. In addition, the compounds of the present invention were also shown to decrease the levels of apoprotein B (apo B) which is the main protein of LDL and the main ligand for LDL receptors. The mechanism of this decrease in apo B and in apo B-associated LDL does not involve inhibition of cholesterol synthesis, which is the mechanism demonstrated for the statins. Therefore, compounds of the present invention are useful for lowering cholesterol in patients who are resistant to treatment with a statin, and, conversely, also have a synergistic effect for lowering cholesterol in those patients who are responding to treatment with statins.

Thus, compounds of the present invention are of use in therapy as cholesterol lowering agents. Furthermore, because of their dual profile in lowering plasma Lp(a) and plasma cholesterol, compounds of formula (I) are of use in therapy for the prevention and/or treatment of both the acute and chronic aspects of atherosclerosis.

Compounds of the present invention may also be of use in preventing and/or treating the above mentioned disease states in combination with anti-hyperlipidaemic, anti-atherosclerotic, anti-diabetic, anti-anginal, anti-inflammatory or anti-hypertension agents. Examples of the above include cholesterol synthesis inhibitors such as statins, for instance atorvastatin, simvastatin, pravastatin, cerivastatin, fluvastatin, lovastatin and ZD 4522 (also referred to as S-4522, Astra Zeneca), anti-oxidants such as probucol, insulin sensitisers such as a PPAR gamma activator, for instance G1262570 (Glaxo Wellcome) and the glitazone class of compounds such as rosiglitazone (Avandia, SmithKline Beecham), troglitazone and pioglitazone, calcium channel antagonists, and anti-inflammatory drugs such as NSAIDs.

For therapeutic use the compounds of the present invention will generally be administered in a standard pharmaceutical composition. Accordingly in a further aspect, the invention provides for a pharmaceutical composition comprising a compound of formula (I) or a pharmaceutically acceptable salt thereof and a pharmaceutically acceptable excipient or carrier. Suitable excipients and carriers are well known in the art and will be selected with regard to the intended route of administration and standard pharmaceutical practice. For example, the compositions may be administered orally in the form of tablets containing such excipients as starch or lactose, or in capsules, ovules or lozenges either alone or in admixture with excipients, or in the form of elixirs or suspensions containing flavoring or coloring agents. They may be injected parenterally, for example, intravenously, intramuscularly or subcutaneously. For parenteral administration, they are best used in the form of a sterile aqueous solution which may contain other substances, for "example, enough salts or glucose to make the solution isotonic with blood. The choice of form for administration as well as effective dosages will vary depending, inter alia, on the condition being treated. The choice of mode of administration and dosage is within the skill of the art.

The compounds of formula (I) and their pharmaceutically acceptable salts which are active when given orally can be formulated as liquids, for example syrups, suspensions or emulsions or as solids for example, tablets, capsules and lozenges. A liquid formulation will generally consist of a suspension or solution of the compound or pharmaceutically acceptable salt in suitable liquid carrier(s) for example, ethanol, glycerine, non-aqueous solvent, for example polyethylene glycol, oils, or water with a suspending agent, preservative, flavoring or coloring agents. A composition in the form of a tablet can be prepared using any suitable pharmaceutical carrier(s) routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration. A typical suppository formulation comprises a compound of structure (I) or a pharmaceutically acceptable salt thereof which is active when administered in this way, with a binding and/or lubricating agent such as polymeric glycols, gelatins or cocoa butter or other low melting vegetable or synthetic waxes or fats. Preferably the composition is in unit dose form such as a tablet or capsule.

Each dosage unit for oral administration contains preferably from 1 to 250 mg (and for parenteral administration contains preferably from 0.1 to 25 mg) of a compound of formula (1) or a pharmaceutically acceptable salt thereof calculated as the free base.

The compounds of the invention will normally be administered to a subject in a daily dosage regimen. For an adult patient this may be, for example, an oral dose of between 1 mg and 500 mg, preferably between 1 mg and 250 mg, or an intravenous, subcutaneous, or intramuscular dose of between 0.1 mg and 100 mg, preferably between 0.1 mg and 25 mg, of the compound of the formula (I) or a pharmaceutically acceptable salt thereof calculated as the free base, the compound being administered 1 to 4 times per day.

The present invention also relates to a process for preparing novel α-substituted-β-aminoethylphosphonate derivatives of formula (I), which is described below.

Compounds of formula (Ib) may be prepared by a process which comprises treating a phosphonate of formula (II):

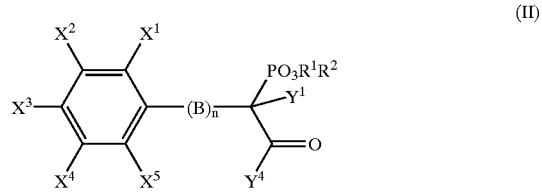

(II)

in which $Y^1$, $X^1$, $X^2$, $X^3$, $X^4$, $X^5$, B, n, $R^1$ and $R^2$ are as previously defined and $Y^4$ is hydrogen or $C_1$–$C_4$ alkyl; with an amine of formula (III):

$$H_2N-(CH_2)_m-Het \qquad (III)$$

in which m and Het are as previously defined,

The coupling reaction between (II) and (III) can be carried out in several ways. In the first variant the phosphonate (II) is condensed with the amine (III) under imine forming conditions. Suitably, the condensation may be effected with or without a catalyst in a solvent such as ether, tetrahydrofuran, benzene, toluene, ethanol or glacial acetic acid. Suitable catalysts include molecular sieve, magnesium sulfate, trialkyl orthoformate, an acid such as glacial acetic acid, p-toluenesulfonic acid, thionyl chloride, titanium tetrachloride, boron trifluoride etherate, or a base such as potassium carbonate. The reaction is suitably carried out in the range of 0° C. to the boiling point of the solvent being used. A particularly advantageous procedure consists in heating to reflux a toluene mixture of equimolar amounts of phosphonate (II) and amine (III) with concomitant elimination of water in a Dean-Stark apparatus. Another variant consists in heating a mixture of equimolar amounts of (II) and (III) in glacial acetic acid at a temperature between room temperature and boiling point, preferably at 40° C. In the third variant, the reaction between the phosphonate (II) and the amine (III) is carried out in presence of hydrogen and a catalyst in a hydrogenation apparatus. Suitable catalysts include Raney Nickel and suitable solvents include acetic acid and the suitable hydrogenation conditions include atmospheric pressure at room temperature.

Both of the first two mentioned variants of the condensation of a phosphonate of formula (II) with an amine of formula (III) afford compounds of formula (Ib). The two isomers can be separated by column chromatography and recrystallization. The structures of these isomers are ascertained by spectroscopic means, MS and in particular NMR, thanks to the characteristic absorption of the olefinic proton. In the (Z)-isomer, the olefinic proton displays a large coupling constant, J=ca 40–43 Hz, due to the trans H—C=C—P coupling. In the (E)-isomer, this value is much smaller, J=15 Hz, due to the cis H—C=C—P coupling.

Compounds of formula (Ia) in which one of $Y^2$ and $Y^3$ is hydrogen can be prepared by reducing the double bond of compounds of formula (Ib). A convenient reduction method is the catalytic hydrogenation using palladium or platinum adsorbed on charcoal as catalysts in a solvent such as ethanol or acetic acid at a pressure between 1 and 4 atm and a temperature between room temperature and 40° C. The reduction can also be carried out by means of a complex hydride reagent such as sodium borohydride or sodium cyanoborohydride in a polar solvent such as methanol, ethanol, isopropanol or n-propanol at a temperature between room and reflux temperature. A further convenient reduction method is the use of a zinc modified sodium cyanoborohydride reagent generated from a mixture of $NaBH_3CN$: $ZnCl_2$ in a 2:1 molar ratio in a solvent selected from diethyl ether, tetrahydrofuran, dimethoxyethane and methanol at a temperature between room temperature and reflux temperature; the reaction can be accelerated by the addition of a higher boiling solvent selected from ethanol, isopropanol, n-propanol, isobutanol or n-butanol and heating to reflux the resulting mixture.

The phosphonate of formula (II) may be prepared by reacting the corresponding phosphonate of formula (IV):

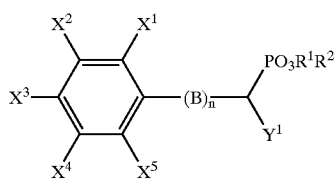

(IV)

in which $Y^1$, $X^1$, $X^2$, $X^3$, $X^4$, $X^5$, B, n, $R^1$ and $R^2$ are as previously defined, with ethyl formate (if $Y^4$ is hydrogen) or with a carboxylic acid derivative $Y^4$—CO—T where $Y^4$ is $C_1$–$C_4$ alkyl as previously defined and T is O-($C_1$–$C_4$ alkyl), halogen (F, Cl, Br, I) or —OO$Y^4$ (wherein $Y^4$ is $C_1$–$C_4$ alkyl), under alkaline conditions. Suitable conditions comprise reacting the phosphonate (IV) with a strong base, for instance n-butyllithium or lithium diisopropylamide in a solvent such as tetrahydrofuran at a temperature between −78° C. to 0° C.

A compound of formula (IV) in which $Y^1$ is $C_1$–$C_4$ alkyl may be readily prepared from a corresponding compound of formula (IV) in which $Y^1$ is hydrogen by the alkylation thereof, for instance using a combination of n-butyl lithium and a $C_1$–$C_4$ alkyl iodide, protecting if necessary any hydroxyl groups on the phenyl ring.

When any of the substituents $X^1$, $X^2$, $X^3$, $X^4$, $X^5$ is a hydroxy group, giving a reactive phenol hydroxy group, it may be useful to protect such a hydroxy group, to avoid troublesome side reactions which may otherwise occur under the strongly alkaline reaction conditions employed. A particularly effective way of protecting the OH group is to convert it into an alkyl silyl ether, such as trimethyl silyl ether ($Me_3Si$ ether or Tms ether) or a t-butyldimethyl silyl ether ($tBuMe_2Si$ ether or Tbs ether). An integral part of this invention is the conversion of a phosphonate of formula (IV) comprising a hydroxy group into the corresponding Tbs ether. Suitable protection reaction conditions are the use of t-butyldimethylsilyl chloride in presence of imidazole in dimethylformamide. Such a Tbs protected phosphonate (IV) then undergoes the addition of ethyl formate (if $Y^4$ is hydrogen) or a carboxylic acid derivative (if $Y^4$ is $C_1$–$C_4$ alkyl) under strongly alkaline conditions to form a Tbs protected phosphonate (V). The Tbs protecting group can then be cleaved by fluoride reagents well established in the art to yield the phosphonate (II) wherein any of the substituents $X^1$, $X^2$, $X^3$, $X^4$, $X^5$ can be a hydroxy group. Suitable deprotection reaction conditions involve reacting the Tbs protected compound with tetrabutyl ammonium fluoride in glacial acetic acid.

Such protection is not however always necessary and the reactive phenol hydroxy group is addressed by using a further equivalent of base and a final acid work up, to convert the "phenolate" back to a "phenol".

The phosphonate of formula (IV) is prepared from commercially available compounds by well established methods.

The invention is further described in the following examples which are intended to illustrate the invention without limiting its scope. The abbreviations used in this application are the following:

In the tables, "n" is normal, "i" is iso, "s" is secondary and "t" is tertiary. In the description of the NMR spectra, respectively "s" is singlet, "d" doublet, "dd" double doublet, "t" triplet, "q" quadruplet and "m" multiplet. TsOH is p-toluenesulfonic acid monohydrate. The temperatures were recorded in degrees Celsius and the melting points are not corrected.

The structures of compounds described in the Examples were established by their infrared (IR), mass (MS) and nuclear magnetic resonance (NMR) spectra. The purity of the compounds was checked by thin layer, gas liquid or high performance liquid chromatographies.

EXAMPLES OF THE INVENTION

Example 1

(Z)- and (E)-Diethyl α-(3,5-dimethoxy-4-hydroxyphenyl)-β-[N-(3-pyridyl)-amino]-vinylphosphonate

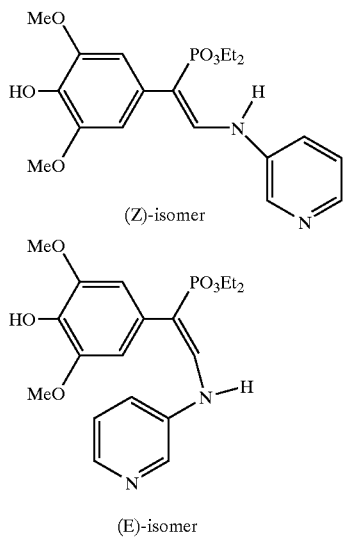

2,6-Dimethoxyphenol (70 g, 0.45 mol) dissolved in 150 ml ethanol was added dropwise to a mixture of formaldehyde (68.5 ml of a 37.5% aqueous solution, 0.91 mol) and dimethylamine (148 ml of a 40% aqueous solution, 1 mol) and the resulting mixture was refluxed for 4 h. Ethanol was evaporated, the residue was partitioned between water and dichloromethane, the organic phase was dried over $MgSO_4$ and evaporated to yield 95 g (99%) of a white solid, mp=78–80° C. To a dioxane solution (600 ml) of the dimethyl(3,5-dimethoxy-4-hydroxybenzyl)amine thus obtained (95 g, 0.45 mol) was added methyl iodide (61 ml, 0.98 mol) and the resulting mixture was refluxed for 2 h. The solid formed was filtered and washed with dioxane to yield 156 g (99%) of the trimethyl(3,5-dimethoxy-4-hydroxybenzyl)ammonium iodide salt. This latter was suspended in 600 ml xylene, triethyl phosphite (110 ml, 0.66 mol) was added dropwise and the resulting mixture was refluxed for 16 h. The solid formed was filtered and the solvent and excess of phosphite were evaporated under vacuum to yield diethyl (3,5-dimethoxy-4-hydroxybenzyl) phosphonate as a viscous oil (130 g, 97%).

Imidazole (58.2 g, 0.86 mol) was added portionwise to a well stirred mixture of the previous compound (130 g, 0.43 mol) and t-butyldimethylsilyl chloride (96.5 g, 0.64 mol) in 400 ml N,N-dimethylformamide (DMF) and stirring was continued for 16 h at room temperature. The mixture was poured into water kept at 0° C. to which was added a 25% ammonium hydroxide solution until pH 7 was reached. The aqueous phase was extracted with dichloromethane, the organic phase was dried over $MgSO_4$. Evaporation of the solvent gave 170 g (95%) of diethyl (4-t-butyldimethylsilyloxy-3,5-dimethoxybenzyl)phosphonate as a dark oil. Under a nitrogen atmosphere n-butyllithium (764 ml of a 1.6 M solution in hexane, 1.22 mol) was added dropwise to 420 ml of dry THF kept at −78° C. Diisopropylamine (123 g, 1.22 mol) was added, the mixture was stirred for 15 min at −78° C. then a solution of diethyl (4-t-butyldimethylsilyloxy-3,5-dimethoxybenzyl) phosphonate (170 g, 0.41 mol) in 50 ml dry THF was added dropwise. After 15 min stirring at −78° C. ethyl formate (75.4 g, 1.02 mol) was added and the resulting mixture was stirred at −78° C. for 1 h. A GLC check of a reaction sample showed that the silylated phosphonate has reacted completely; the reaction temperature was left to reach −30° C. then hydrolysis was carried out with a saturated ammonium chloride solution. The quenched reaction mixture was extracted with diethyl ether, the ether extract was dried over $MgSO_4$, filtered and evaporated to dryness to yield diethyl α-formyl (4-t-butyldimethylsilyloxy-3,5-dimethoxybenzyl) phosphonate as a beige solid (180 g, 99%). The latter compound (180 g, 0.41 mol) and tetrabutylammonium fluoride trihydrate (TBAF) (513 g, 1.63 mol) were placed in 400 ml THF to which were added dropwise glacial acetic acid (293 g, 4.89 mol). After stirring at 20° C. overnight a GLC test showed that the Tbs protected compound has entirely reacted. The reaction mixture was extracted with dichloromethane, the organic phase was washed with a saturated bicarbonate solution, dried over $MgSO_4$. The residue of the evaporated extract was purified by column chromatography (silica gel, 9/1 $CH_2Cl_2$/MeOH). The pure fractions gave 95 g (71%) of diethyl α-formyl (3,5-dimethoxy-4-hydroxybenzyl)phosphonate as a oil.

To a mixture of the previous compound (15 g, 45 mmol) and 3-aminopyridine (4.15 g, 45 mmol) in 120 ml acetic acid placed in a hydrogenation vessel were cautiously added 120 ml of an aqueous suspension of Raney-Nickel and the resulting mixture was hydrogenated for 16 h in a Parr apparatus. The catalyst was filtered, the solution was extracted with dichloromethane, the organic phase was washed with a bicarbonate solution and dried over $MgSO_4$. The residue after evaporation was purified by column chromatography (silica gel, 9/1 $CH_2Cl_2$/MeOH) to give 2 g (11%) of (Z)-diethyl α-(3,5-dimethoxy-4-hydroxyphenyl)-β-[N-(3-pyridyl)-amino]-vinylphosphonate and 11 g (60%) of (E)-diethyl α-(3,5-dimethoxy-4-hydroxyphenyl)-β-[N-(3-pyridyl)-amino]-vinylphosphonate.
Physico-Chemical and Spectroscopic Data:
(Z)-diethyl α-(3,5-dimethoxy-4-hydroxyphenyl)-β-[N-(3-pyridyl)-amino]-vinylphosphonate.
  Mp=173–174° C. (ligroine/ethanol)
  MS (m/e)=408 (100%): M⁺, 270: M⁺ —$HPO_3Et_2$.
  NMR ($CDCl_3$)=δ=9.89 (d, 1H, J=13 Hz): N—H 8.36, 8.21, 7.27–7.19 (4 m, 1H each): aromatic H, 3-pyridyl 7.5 (dd, 1H, J=13 and 41 Hz): (Ph)(P)C=CH—NH-Pyridine 6.61 (s, 2H): aromatic H, substituted phenyl 5.66 (s, 1H): OH 4.2–4.0 (m, 4H): P—O—CH₂—CH₃ 3.91 (s, 6H): Ph-OCH₃ 1.30 (t, J=7 Hz): P—O—CH₂—CH₃.
(E)-diethyl α-(3,5-dimethoxy-4-hydroxyphenyl)-β-[N-(3-pyridyl)-amino]-vinylphosphonate.
  Mp=201–203° C. (ligroine/ethanol)
  MS (m/e)=408 (100%): M⁺, 270: M⁺ —$HPO_3Et_2$.
  NMR ($CDCl_3$)=δ=8.2, 7.32 and 7.22 (3 m, 4H total): aromatic H, 3-pyridyl 7.7 (dd, 1H, J=13 and 15 Hz): (Ph)(P)C=CH—NH-pyridine 6.58 (d, 1H each, J=2 Hz): aromatic H, substituted phenyl 6.49 (d, 1H, J=13 Hz): N—H 5.76 (s, 1H): OH 4.15–4.05 (m, 4H): P—O—CH₂—CH₃ 3.90 (s, 6H): Ph-OCH₃ 1.30 (t, J=7 Hz): P—O—CH₂—CH₃.

Example 2

Diethyl α-(3,5-dimethoxy-4-hydroxyphenyl)-β-[N-(3-pyridyl)-amino]-ethylphosphonate

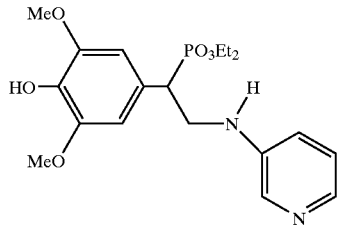

Sodium cyanoborohydride (7.7 g, 123 mmol) was added to a mixture of (Z)- and (E)-diethyl α-(3,5-dimethoxy-4-hydroxyphenyl)-β-[N-(3-pyridyl)-amino]-vinylphosphonate (10 g, 24.5 mmol) dissolved in 50 ml acetic acid and the mixture was stirred for 72 h at room temperature. The mixture was neutralized with a 10% sodium hydroxide solution, extracted with dichloromethane, dried and evaporated. Column chromatography (silica gel, 9/1 $CH_2Cl_2$/MeOH) gave 3 g (30%) of the title compound.

Physico-Chemical and Spectroscopic Data:

Mp 152–154° C. (ligroine/ethanol)

MS (m/e)=410: M⁺, 304 (100%): M⁺ —$CH_2$—NH—$C_5H_4N$

NMR ($CDCl_3$): δ=8.0, 7.10 and 6.88 (3 m, 4H total): aromatic H, 3-pyridyl 6.56 (d, J=2 Hz, 2H): aromatic H, substituted phenyl 5.86 (s, 1H): OH 4.2–3.9 (m, 4H): P—O—CH₂—CH₃ 3.87 (s, 6H): Ph-OCH₃ 3.8–3.55 (m, 2H): (Ph)(P)CH—CH₂—NH-pyridine 3.34–3.24 (m, 1H): (Ph)(P)CH—CH₂—NH-pyridine 1.35 and 1.14 (2 t, J=7 Hz): P—O—CH₂—CH₃.

Example 3

(Z)- and (E)-Diethyl α-(4-hydroxy-3-methoxy-5-methylphenyl)-β-[N-(3-(2,6-dimethylpyridyl))-amino]-vinylphosphonate

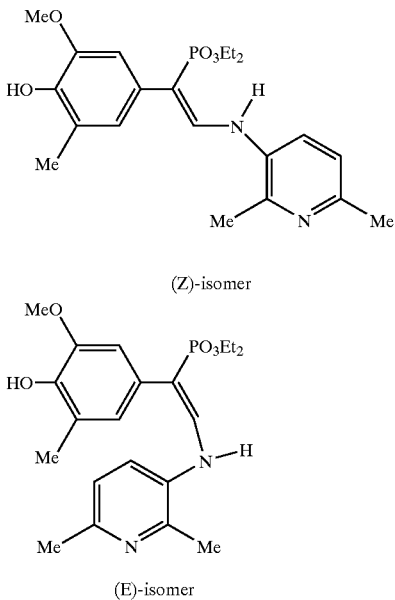

(Z)-isomer (E)-isomer

Step 1—Dimethyl(4-hydroxy-3-methoxy-5-methylbenzyl) amine:

2-Methoxy-6-methylphenol (70 g, 0.51 mol) dissolved in 150 ml ethanol was added dropwise to a mixture of formaldehyde (76.5 ml of a 37.5% aqueous solution, 1.01 mol) and dimethylamine (165 ml of a 40% aqueous solution, 1.12 mol) and the resulting mixture was refluxed for 4 h. Ethanol was evaporated, the residue was partitioned between water and dichloromethane, the organic phase was dried over MgSO$_4$ and evaporated to yield 98 g (99%) of the subtitle compound as a white solid.

Step 2—Trimethyl(4-hydroxy-3-methoxy-5-methylbenzyl) ammonium Iodide:

To a dioxane solution (600 ml) of dimethyl(4-hydroxy-3-methoxy-5-methylbenzyl)amine (98 g, 0.50 mol) was added methyl iodide (69 ml, 1.11 mol) and the resulting mixture was refluxed for 2 h. The solid formed was filtered and washed with dioxane to yield 165 g (98%) of the trimethyl(4-hydroxy-3-methoxy-5-methylbenzyl) ammonium iodide salt.

Step 3—Diethyl(4-hydroxy-3-methoxy-5-methylbenzyl) phosphonate:

The iodide obtained in step 2 (165 g, 0.49 mol) was suspended in 600 ml xylene, triethyl phosphite (122 ml, 0.70 mol) was added dropwise and the resulting mixture was refluxed for 16 h. The solid formed was filtered and the solvent and excess of phosphite were evaporated under vacuum to yield diethyl (4-hydroxy-3-methoxy-5-methylbenzyl)phosphonate as a viscous oil (128 g, 95%).

Step 4-a—Diethyl α-formyl (4-hydroxy-3-methoxy-5-methylbenzyl)phosphonate:

Imidazole (60.3 g, 0.89 mol) was added portionwise to a well stirred mixture of the previous compound (128 g, 0.44 mol) and t-butyldimethylsilyl chloride (100 g, 0.66 mol) in 400 ml DMF and stirring was continued for 16 h at room temperature. The mixture was poured into water kept at 0° C. to which was added a 25% ammonium hydroxide solution until pH 7 was reached. The aqueous phase was extracted with dichloromethane, the organic phase was dried over MgSO$_4$. Evaporation of the solvent gave 178 g (100%) of diethyl (4-t-butyldimethylsilyloxy-3-methoxy-5-methylbenzyl)phosphonate as a dark oil. Under a nitrogen atmosphere n-butyllithium (830 ml of a 1.6 M solution in hexane, 1.33 mol) was added dropwise to 420 ml of dry THF kept at −78° C. Diisopropylamine (134 g, 1.33 mol) was added, the mixture was stirred for 15 min at −78° C. then a solution of diethyl (4-t-butyldimethylsilyloxy-3-methoxy-5-methylbenzyl)phosphonate (178 g, 0.44 mol) in 50 ml dry THF was added dropwise. After 15 min stirring at −78° C. ethyl formate (82 g, 1.11 mol) was added and the resulting mixture was stirred at −78° C. for 1 h. A GLC check of a reaction sample showed that the silylated phosphonate has reacted completely; the reaction temperature was left to reach −30° C. then hydrolysis was carried out with a saturated ammonium chloride solution. The quenched reaction mixture was extracted with diethyl ether, the ether extract was dried over MgSO$_4$, filtered and evaporated to dryness to yield diethyl α-formyl (4-t-butyldimethylsilyloxy-3-methoxy-5-methylbenzyl) phosphonate as a beige solid (175 g, 92%). The previous compound (175 g, 0.41 mol) and TBAF (513 g, 1.63 mol) were placed in 400 ml THF to which were added dropwise glacial acetic acid (293 g, 4.89 mol). After stirring at 20° C. overnight a GLC test showed that the Tbs protected compound has entirely reacted. The reaction mixture was extracted with dichloromethane, the organic phase was washed with a saturated bicarbonate solution, dried over MgSO$_4$. The residue of the evaporated extract was purified by column chromatography (silica gel, 9/1 CH$_2$Cl$_2$/MeOH). The pure fractions gave 96 g (75%) of diethyl α-formyl (4-hydroxy-3-methoxy-5-methylbenzyl)phosphonate as a brown oil. Crystallisation from methyl t-butyl ether gave a white solid, mp 85–86° C.

Step 4-b—Diethyl α-formyl (4-hydroxy-3-methoxy-5-methylbenzyl)phosphonate (Alternative to Step 4-a):

A solution of diethyl (4-hydroxy-3-methoxy-5-methylbenzyl)phosphonate (26 g, 0.090 mol) in THF (650 ml) was cooled to −70° C. A solution of n-butyl lithium (90 ml of 2.5 M solution in hexanes, 0.225 mol) was added over 15 min. The resulting thick suspension was stirred for a further 30 min at −70° C. A solution of ethyl formate (30 ml, 0.37 mol) in THF (50 ml) was added over 10 min and the mixture stirred for a further 10 min at −70° C., then saturated aqueous ammonium chloride (600 ml) was added and the mixture allowed to warm to room temperature. Diethyl ether and water were added, the organic phase was washed with brine, then dried over MgSO$_4$. The residue of the evaporated extract was purified by column chromatography (silica gel, ethylacetate). The pure fractions gave 24 g (84%) of diethyl α-formyl (4-hydroxy-3-methoxy-5-methylbenzyl) phosphonate as a brown oil.

Step 5—(Z)- and (E)-Diethyl α-(4-hydroxy-3-methoxy-5-methylphenyl)-β-[N-(3-(2,6-dimethylpyridyl))-amino]-vinylphosphonate:

A mixture of diethyl α-formyl (4-hydroxy-3-methoxy-5-methylbenzyl)phosphonate (20 g, 63 mmol) and 2,6-dimethyl-3-aminopyridine (7.5 g, 62 mmol) in 120 ml acetic acid was warmed to 40° C. for 4 h. The cooled solution was neutralized first with a 20% NaOH then a saturated sodium bicarbonate solution, extracted with dichloromethane and the organic phase was dried over MgSO$_4$. The residue after evaporation was purified by column chromatography (silica gel, 9/1 AcOEt/MeOH) to give 10 g (39%) of (Z)-diethyl α-(4-hydroxy-3-methoxy-5-methylphenyl)-β-[N-(3-(2,6-dimethylpyridyl))-amino]-vinylphosphonate and 11.5 g (44%) of (E)-diethyl α-(4-hydroxy-3-methoxy-5-methylphenyl)-β-[N-(3-(2,6-dimethylpyridyl))-amino]-vinylphosphonate.
Physico-Chemical and Spectroscopic Data:
(Z)-diethyl α-(4-hydroxy-3-methoxy-5-methylphenyl)-β-[N-(3-(2,6-dimethylpyridyl))-amino]-vinylphosphonate
Mp=136–138° C. (ligroine/ethanol)
MS (m/e)=420 (100%): M$^+$, 282: M$^+$ —HPO$_3$Et$_2$.
NMR (CDCl$_3$)=δ=9.87 (d, 1H, J=13 Hz): N—H 7.45 (dd, 1H, J=13 and 41.5 Hz): (Ph)(P)C=C$\underline{H}$—NH-pyridine 7.16 and 6.94 (2 d, J=9 Hz, 2H): aromatic H, 3-pyridyl 6.8 and 6.7 (2 s, 2H): aromatic H, substituted phenyl 5.66 (s, 1H): O$\underline{H}$ 4.2–4.0 (m, 4H): P—O—C$\underline{H}_2$—CH$_3$ 3.89 (s, 3H): Ph-OC$\underline{H}_3$ 2.56 and 2.48 (2 s, 6H total): Py-C$\underline{H}_3$ 2.27 (is, 3H): Ph-C$\underline{H}_3$ 1.30 (t, J=7 Hz): P—O—CH$_2$—C$\underline{H}_3$.
(E)-diethyl α-(4-hydroxy-3-methoxy-5-methylphenyl)-β-[N-(3-(2,6-dimethylpyridyl))-amino]-vinylphosphonate
Mp=136–138° C. (ligroine/ethanol)
MS (m/e)=420 (100%): M$^+$, 282: M$^+$ —HPO$_3$Et$_2$.
NMR (CDCl$_3$)=δ=7.66 (dd, 1H, J=13 and 15 Hz): (Ph)(P)C=C$\underline{H}$—NH-pyridine 7.32 and 6.96 (2 d, J=9 Hz, 2H): aromatic H, 3-pyridyl 6.78 and 6.77 (2 s, 2H): aromatic H, substituted phenyl 6.43 (d, 1H, J=13 Hz): N—H 5.84 (s, 1H): O$\underline{H}$ 4.14–4.04 (m, 4H): P—O—C$\underline{H}_2$—CH$_3$ 3.88 (s, 3H): Ph-OC$\underline{H}_3$ 2.45 and 2.28 (2 s, 6H total): Py-C$\underline{H}_3$ 2.26 (is, 3H): Ph-C$\underline{H}_3$ 1.30 (t, J=7 Hz): P—O—CH$_2$—C$\underline{H}_3$.

Example 4

Diethyl α-(4-hydroxy-3-methoxy-5-methylphenyl)-β-[N-(3-(2,6-dimethylpyridyl))-amino]-ethylphosphonate

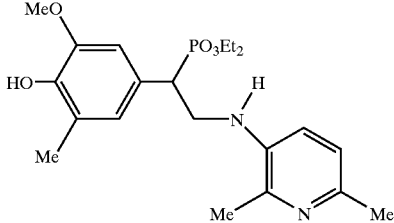

10% Palladium on activated charcoal (10 g) was added to a mixture of (Z)- and (E)-diethyl α-(4-hydroxy-3-methoxy-5-methylphenyl)-β-[N-(3-(2,6-dimethylpyridyl))-amino]-vinylphosphonate (28 g, 61 mmol) dissolved in 50 ml acetic acid and the mixture was submitted to hydrogenation under atmospheric pressure in a Parr apparatus for 72 h at room temperature. The mixture was neutralized with a 10% sodium hydroxide solution, extracted with dichloromethane, dried and evaporated. Column chromatography (silica gel, 9/1 CH$_2$Cl$_2$/MeOH and 9/1 AcOEt/EtOH) gave 16 g (62%) of the title compound as a viscous oil which slowly solidified. Trituration in petroleum ether gave a colourless solid, mp=82–85° C. Recrystallisation from methyl tert-butyl ether gave a colourless solid, mp=93.0–93.5° C.
Physico-Chemical and Spectroscopic Data:
MS (m/e)=422: M$^+$, 288: M$^+$ —CH$_2$—NH—C$_7$H$_8$N, 135 (100%)
NMR (CDCl$_3$): δ=6.90 and 6.83 (2 d, J=9 Hz, 2H): aromatic H, 3-pyridyl 6.73 and 6.86 (2 m, 2H): aromatic H, substituted phenyl 5.76 (broad, 1H): N—H 5.3 (s, 1H): O$\underline{H}$ 4.2–3.9 (m, 4H): P—O—C$\underline{H}_2$—CH$_3$ 3.85 (s, 3H): Ph-OCH$_3$ 3.85–3.75 and 3.58–3.46 (2 m, 2H): (Ph)(P)CH—C$\underline{H}_2$—NH-pyridine 3.31–3.21 (m, 1H): (Ph)(P)C$\underline{H}$—CH$_2$—NH-pyridine 2.42 and 2.23 (2 s, 6H total): Py-C$\underline{H}_3$ 2.18 (1 s, 3H): Ph-C$\underline{H}_3$ 1.33 and 1.15 (2 t, J=7 Hz, 6H total): P—O—CH$_2$—C$\underline{H}_3$.

Example 5

(Z)- and (E)-Diethyl α-(4-hydroxy-3-methoxy-5-methylphenyl)-β-[N-(pyrazinyl)-amino]-vinylphosphonate

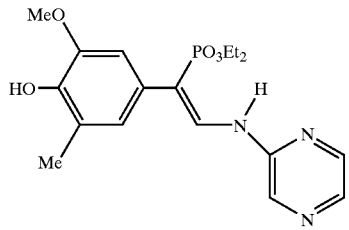

(Z)-isomer

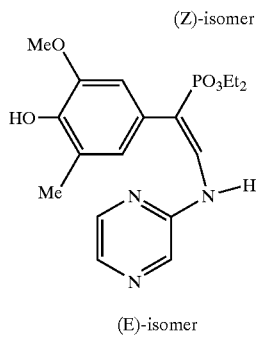

(E)-isomer

A mixture of diethyl α-formyl (4-hydroxy-3-methoxy-5-methylbenzyl)phosphonate (11.4 g, 36.2 mmol), aminopyrazine (3.45 g, 36.2 mmol) and 5 mg of p-toluenesulfonic acid monohydrate (TsOH) dissolved in 90 ml toluene connected to a Dean-Stark apparatus was refluxed for 8 h. The solvent was evaporated to dryness and the residue was purified by column chromatography (silica gel, 95/5 CH$_2$Cl$_2$/MeOH) to give 4.5 g (11.5 mmol, 32%) of (Z)-diethyl α-(4-hydroxy-3-methoxy-5-methylphenyl)-β-[N-(pyrazinyl)-amino]-vinylphosphonate and 0.5 g (1.3 mmol, 4%) of (E)-diethyl α-(4-hydroxy-3-methoxy-5-methylphenyl)-β-[N-(pyrazinyl)-amino]-vinylphosphonate.
Physico-Chemical and Spectroscopic Data:
(Z)-Diethyl α-(4-hydroxy-3-methoxy-5-methylphenyl)-β-[N-(pyrazinyl)-amino]-vinylphosphonate
Mp=136–138° C.
MS (m/e)=393: M$^+$, 256 (100%): M$^+$ —PO$_3$Et$_2$.
NMR (CDCl$_3$)=δ=10.48 (d, 1H, J=12 Hz): N—H 8.22 (dd, 1H, J=12 and 43 Hz): (Ph)(P)C=C$\underline{H}$—NH-pyrazine 8.15, 8.12 and 8.05 (3 m, 1H each): aromatic H, pyrazinyl 6.82 and 6.78 (2 s, 2H): aromatic H, substituted phenyl 5.7 (s, 1H): O$\underline{H}$ 4.2–4.0 (m, 4H): P—O—C$\underline{H}_2$—CH$_3$ 3.89 (s, 3H): Ph-OC$\underline{H}_3$ 2.27 (is, 3H): Ph-C$\underline{H}_3$ 1.31 (t, J=7 Hz): P—O—CH$_2$—C$\underline{H}_3$.
(E)-Diethyl α-(4-hydroxy-3-methoxy-5-methylphenyl)-β-[N-(pyrazinyl)-amino]-vinylphosphonate.
Mp=174–176° C.
MS (m/e)=393: M$^+$, 256 (100%): M$^+$ —PO$_3$Et$_2$.
NMR (CDCl$_3$)=δ=8.13, 8.12 and 8.09 (3 m, 3H total): aromatic H, 3-pyrazine ca 8.15: (Ph)(P)C=C$\underline{H}$—NH-pyridine 6.93 (d, 1H, J=13 Hz): N—H 6.73 and 6.70 (2 s, 1H each): aromatic H, substituted phenyl 5.86 (s, 1H): O$\underline{H}$ 4.16–4.06 (m, 4H): P—O—C$\underline{H}_2$—CH$_3$ 3.88 (s, 6H): Ph-OC$\underline{H}_3$ 2.28 (1 s, 3H): Ph-C$\underline{H}_3$ 1.31 (t, J=7 Hz): P—O—CH$_2$—C$\underline{H}_3$.

Example 6

Diethyl α-(4-hydroxy-3-methoxy-5-methylphenyl)-β-[N-(pyrazinyl)-amino]-ethylphosphonate

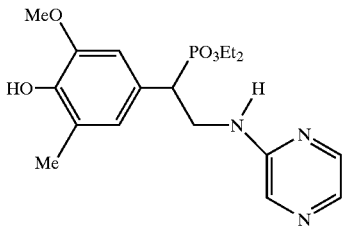

Sodium borohydride (2.9 g, 76 mmol) was added cautiously to a mixture containing 6 g (15.3 mmol) of ca 4/1 of (Z)-/(E)-diethyl α-(4-hydroxy-3-methoxy-5-methylphenyl)-β-[N-(pyrazinyl)-amino]-vinylphosphonate dissolved in 60 ml ethanol. After 24 h at reflux, a further portion (2.9 g) of sodium borohydride was added and the resulting mixture was refluxed for another 24 h period. Ethanol was evaporated, the residue was partitioned between dichloromethane and water, the organic phase was dried and evaporated. The residue after evaporation was purified by column chromatography ($SiO_2$, 9/1 AcOEt/MeOH) to give 1.2 g (22%) of the title compound, Physico-Chemical and Spectroscopic Data:

mp=126–128° C.

MS (m/e) 395: $M^+$, 288 (100%): $M^+$ —$CH_2$—NH—$C_4H_3N$

NMR ($CDCl_3$): δ=7.98 (m, 1H), 7.83 (m, 1H) and 7.80 (d, 1H, J=3 Hz): aromatic H, pyrazine 6.74 and 6.70 (m, 2H): aromatic H, substituted phenyl 5.73 (s, 1H): O$\underline{H}$ 4.99 (t, 1H): N—H 4.15–3.94 (m, 4H): P—O—C$\underline{H}_2$—$CH_3$ 3.87–3.74 (m, 2H): (Ph)(P)CH—C$\underline{H}_2$—NH-pyrazine 3.85 (s, 3H): Ph-OC$\underline{H}_3$ 3.40–3.30 (m, 1H): (Ph)(P)C$\underline{H}$—$CH_2$—NH-pyrazine 2.23 (1 s, 3H): Ph-C$\underline{H}_3$ 1.32 and 1.16 (2 t, J=7 Hz): P—O—$CH_2$—C$\underline{H}_3$.

Example 7

(Z)- and (E)-Diisopropyl α-(3,5-dimethoxy-4-hydroxyphenyl)-β-[N-(2-pyrimidinyl)-amino]-vinylphosphonate

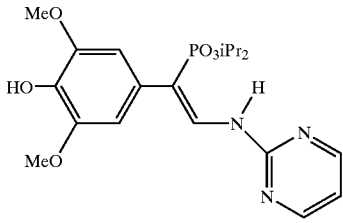

(Z)-isomer

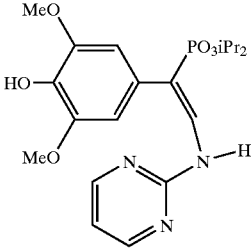

(E)-isomer

A mixture of diisopropyl α-formyl (3,5-dimethoxy-4-hydroxybenzyl)phosphonate (12.0 g, 33.3 mmol), 2-aminopyrimidine (3.17 g, 33.3 mmol) and 5 mg of TsOH dissolved in 90 ml toluene connected to a Dean-Stark apparatus was refluxed for 8 h. The solvent was evaporated to dryness and the residue was purified by column chromatography (silica gel, 9/1 AcOEt/MeOH and 95/1 $CH_2Cl_2$/MeOH) to give 4.1 g (9.4 mmol, 28%) of (Z)-diisopropyl α-(3,5-dimethoxy-4-hydroxyphenyl)-β-[N-2-(pyrimidinyl)-amino]-vinylphosphonate and 0.7 g (1.6 mmol, 5%) of (E)-diisopropyl α-(3,5-dimethoxy-4-hydroxyphenyl)-β-[N-(2-pyrimidinyl)-amino]-vinylphosphonate.

Physico-Chemical and Spectroscopic Data:

(Z)-Diisopropyl α-(3,5-dimethoxy-4-hydroxyphenyl)-β-[N-(2-pyrimidinyl)-amino]-vinylphosphonate Mp=121–122° C.

MS (m/e)=437: $M^+$, 272 (100%): $M^+$ —$HPO_3iPr_2$.

NMR ($CDCl_3$)=δ=10.6 (d, 1H, J=12 Hz): N—H 8.42 (d, J=5 Hz, 2H) and 6.79 (t, J=5 Hz, 1H): aromatic H, 2-pyrimidine 8.22 (dd, 1H, J=12 and 43 Hz): (Ph)(P)C=C$\underline{H}$—NH-pyrimidine 6.71 (d, J=2 Hz, 2H): aromatic H, substituted phenyl 5.54 (s, 1H): O$\underline{H}$ 4.74–4.64 (m, 2H): P—O—C$\underline{H}$—($CH_3$)$_2$ 3.90 (s, 6H): Ph-OC$\underline{H}_3$ 1.36 and 1.20 (2 d, J=6 Hz, 12H total): P—O—$CH_2$—(C$\underline{H}_3$)$_2$.

(E)-Diisopropyl α-(3,5-dimethoxy-4-hydroxyphenyl)-β-[N-(2-pyrimidinyl)-amino]-vinylphosphonate Mp=168–170° C.

MS (m/e)=437: $M^+$, 272 (100%): $M^+$ —$HPO_3iPr_2$.

NMR ($CDCl_3$)=δ=8.41 (d, J=5 Hz, 2H) and 6.81 (t, J=5 Hz, 1H): aromatic H, 2-pyrimidine 8.33 (dd, 1H, J=13 and 16 Hz): (Ph)(P)C=C$\underline{H}$—NH-pyrimidine 7.55 (d, 1H, J=13 Hz): N—H 6.61 (d, J=2 Hz, 2H): aromatic H, substituted phenyl 4.75–4.65 (m, 2H): P—O—C$\underline{H}_2$—($CH_3$)$_2$ 3.82 (s, 6H): Ph-OC$\underline{H}_3$ 1.32 and 1.26 (2 d, J=6 Hz, 12H total): P—O—$CH_2$—(C$\underline{H}_3$)$_2$.

Example 8

Di-isopropyl α-(3,5-dimethoxy-4-hydroxyphenyl)-β-[N-(2-pyrimidinyl)-amino]-ethylphosphonate

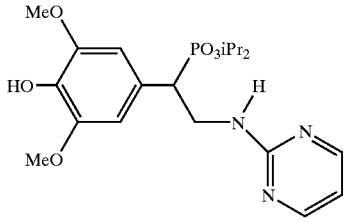

Sodium borohydride (0.65 g, 17.2 mmol) was added cautiously to a mixture containing 1.5 g (3.43 mmol) of (Z)-/(E)-diisopropyl α-(3,5-dimethoxy-4-hydroxyphenyl)-β-[N-(2-pyrimidinyl)-amino]-vinylphosphonate dissolved in 60 ml isopropanol. After 56 h at reflux isopropanol was evaporated, the residue was partitioned between dichloromethane and water, the organic phase was dried and evaporated. The residue after evaporation was purified by column chromatography (SiO$_2$, 9/1 AcOEt/MeOH) to give the title compound.

Physico-Chemical and Spectroscopic Data:

MS (m/e)=439: M$^+$, 332: M$^+$ —CH$_2$—NH—C$_4$H$_3$N$_2$, 248 (100%)

NMR (CDCl$_3$)=δ=8.24 (d, J=5 Hz, 2H) and 6.51 (t, J=5 Hz, 1H): aromatic H, 2-pyrimidine 6.59 (d, J=2 Hz, 2H): aromatic H, substituted phenyl 5.73 (s, 1H): OH 5.32 (t, 1H): N—H 4.74–4.64 and 4.53–4.45 (2 m, 2H): P—O—CH$_2$—(CH$_3$)$_2$ 4.24–4.14 and 3.83–3.73 (m, 2H): (Ph)(P)CH—CH$_2$—NH-pyrimidine 3.34–3.24 (m, 1H): (Ph)(P)CH—CH$_2$—NH-pyrimidine 3.83 (s, 6H): Ph-OCH$_3$ 1.32, 1.31, 1.26 and 0.90 (4 d, J=6 Hz, 12H total): P—O—CH$_2$—(CH$_3$)$_2$.

Example 9

(E)-Diethyl α-(3,5-dimethyl-4-hydroxyphenyl)-β-[N-(5-(2-methylpyridyl))-amino]-vinylphosphonate

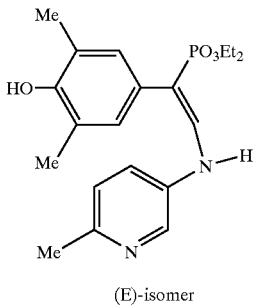

(E)-isomer 2,6-dimethylphenol (112.5 g, 0.92 mol) dissolved in 250 ml ethanol was added dropwise to a mixture of formaldehyde (139 ml of a 36.5% aqueous solution, 1.84 mol) and dimethylamine (300 ml of a 40% aqueous solution, 2.03 mol) and the resulting mixture was refluxed for 4 h. Ethanol was evaporated, the residue was partitioned between water and dichloromethane, the organic phase was dried over MgSO$_4$ and evaporated to yield 165 g (100%) of an oil. To a dioxane solution (900 ml) of the dimethyl(3,5-dimethyl-4-hydroxybenzyl)amine thus obtained (165 g, 0.92 mol) was added methyl iodide (126 ml, 2.03 mol) and the resulting mixture was refluxed for 2 h. The solid formed was filtered and washed with dioxane to yield 296 g (100%) of the trimethyl(3,5-dimethyl-4-hydroxybenzyl)ammonium iodide salt. This latter (148 g, 0.46 mol) was suspended in 300 ml xylene, triethyl phosphite (120 ml, 0.69 mol) was added dropwise and the resulting mixture was refluxed for 16 h. The solid formed was filtered and the solvent and excess of phosphite were evaporated under vacuum to yield diethyl (3,5-dimethyl-4-hydroxybenzyl)phosphonate as a viscous oil (117 g, 93%).

Imidazole (58.5 g, 0.86 mol) was added portionwise to a well stirred mixture of the previous compound (117 g, 0.43 mol) and t-butyldimethylsilyl chloride (97 g, 0.65 mol) in 400 ml DMF and stirring was continued for 16 h at room temperature. The mixture was poured into water kept at 0° C. to which was added a 25% ammonium hydroxide solution until pH 7 was reached. The aqueous phase was extracted with dichloromethane, the organic phase was dried over MgSO$_4$. Evaporation of the solvent gave 158.5 g (95%) of diethyl (4-t-butyldimethylsilyloxy-3,5-dimethyl benzyl) phosphonate as a dark oil. Under a nitrogen atmosphere n-butyllithium (770 ml of a 1.6 M solution in hexane, 1.23 mol) was added dropwise to 400 ml of dry THF kept at −78° C. Diisopropylamine (124 g, 1.23 mol) was added, the mixture was stirred for 15 min at −78° C. then a solution of diethyl (4-t-butyldimethylsilyloxy-3,5-dimethyl benzyl) phosphonate (158.5 g, 0.41 mol) in 50 ml dry THF was added dropwise. After 15 min stirring at −78° C. ethyl formate (76 g, 1.03 mol) was added and the resulting mixture was stirred at −78° C. for 30 min. A GLC check of a reaction sample showed that the silylated phosphonate has reacted completely; the reaction temperature was left to reach −30° C. then hydrolysis was carried out with 300 ml of a saturated ammonium chloride solution. The quenched reaction mixture was extracted with diethyl ether, the ether extract was dried over MgSO$_4$, filtered and evaporated to dryness to yield diethyl α-formyl diethyl (4-t-butyldimethylsilyloxy-3,5-dimethyl benzyl)phosphonate as a beige solid (170 g, 100%). The previous compound (170 g, 0.41 mol) was placed in 400 ml THF to which was added TBAF (388 g, 1.23 mol) dissolved in THF, followed by glacial acetic acid (150 ml, 2.46 mol). After stirring at 20° C. overnight a GLC test showed that the Ths protected compound has entirely reacted. The reaction mixture was extracted with dichloromethane, the organic phase was washed with a saturated bicarbonate solution, dried over MgSO$_4$. The residue of the evaporated extract was purified by column chromatography (silica gel, 95/5 CH$_2$Cl$_2$/MeOH). The pure fractions gave 78 g (60%) of diethyl α-formyl diethyl (3,5-dimethyl-4-hydroxybenzyl) phosphonate as a brown oil.

A mixture of diethyl α-formyl diethyl (3,5-dimethyl-4-hydroxybenzyl)phosphonate (6.5 g, 22 mmol) and 5-amino-2-methylpyridine (2.34 g, 22 mmol) in 30 ml acetic acid was warmed to 40° C. for 4 h. The cooled solution was neutralized with a 20% NaOH, extracted with dichloromethane then the organic phase was dried over MgSO$_4$. Recrystallisation of the residue in a ligroine:dichloromethane:ethanol mixture gave 2.0 g (24%) of (E)-diethyl α-(3,5-dimethyl-4-hydroxyphenyl)-β-[N-(5-(2-methylpyridyl))-amino]-vinylphosphonate. Thin layer chromatography showed the mother liquor (2.6 g, 31%) to contain a mixture of (Z)- and (E)-diethyl α-(3,5-dimethyl-4-hydroxyphenyl)-β-[N-(5-(2-methylpyridyl))-amino]-vinylphosphonate.

(E)-Diethyl α-(3,5-dimethyl-4-hydroxyphenyl)-β-[N-(5-(2-methylpyridyl))-amino]-vinylphosphonate: mp=210–212° C.

Physico-Chemical and Spectroscopic Data:

MS (m/e)=390 (100%): M$^+$, 252: M$^+$ —HPO$_3$Et$_2$.

NMR (CDCl$_3$)=δ=8.04, 7.23 and 7.07 (3 m, 3H total): aromatic H, 3-pyridyl 7.65 (dd, 1H, J=13 and 15 Hz): (Ph)(P)C═CH—NH-pyridine 6.93 (m, 2H): aromatic H, substituted phenyl 6.34 (d, 1H, J=13 Hz): N—H 5.69 (s, 1H): OH 4.15–4.05 (m, 4H): P—O—CH$_2$—CH$_3$ 2.49 (2 s, 3H): Py-CH$_3$ 2.29 (is, 6H): Ph-CH$_3$ 1.30 (t, J=7 Hz): P—O—CH$_2$—CH$_3$.

Example 10

Diethyl α-(3,5-dimethyl-4-hydroxyphenyl)-β-[N-(5-(2-methylpyridyl))-amino]-ethylphosphonate

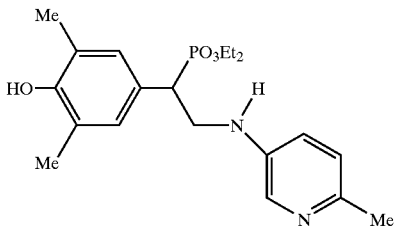

A solution of sodium cyanoborohydride (2.42 g, 38 mmol) and zinc chloride (2.62 g, 19 mmol) in methanol was added to a mixture of (Z)- and (E)-diethyl α-(3,5-dimethyl-4-hydroxyphenyl)-β-[N-(5-(2-methylpyridyl))-amino]-vinylphosphonate (2.6 g, 66 mmol) dissolved in 20 ml methanol and the mixture was refluxed for 16 h. The mixture was partitioned between water and dichloromethane, the organic phase was dried and evaporated. Column chromatography (silica gel, 9/1 AcOEt/MeOH) gave 1.6 g (50%) of the title compound as a viscous oil which slowly solidified.
Physico-Chemical and Spectroscopic Data:
MS (m/e)=392: M$^+$, 272 (100%): M$^+$ —CH$_2$—NH—C$_5$H$_4$N
NMR (CDCl$_3$): δ=7.86, 6.96 and 6.85 (3 m, 3H total): aromatic H, 3-pyridyl 6.92 (d, 2H): aromatic H, substituted phenyl ca 5.8 (broad): OH 4.2–3.8 (m, 4H): P—O—CH$_2$—CH$_3$ ca 3.85–3.75 and 3.3–3.2 (2 m, 2H total): (Ph)(P)CH—CH$_2$—NH-pyridine 3.6–3.5 (m, 1H): (Ph)(P)CH—CH$_2$—NH-pyridine 2.44 (is, 3H): Py-CH$_3$ 2.22 (is, 6H): Ph-CH$_3$ 1.33 and 1.16 (2 t, J=7 Hz): P—O—CH$_2$—CH$_3$.

Example 11

Enantiomers of Diethyl α-(4-hydroxy-3-methoxy-5-methylphenyl)-β-[N-(3-(2,6-dimethylpyridyl))-amino]-ethylphosphonate

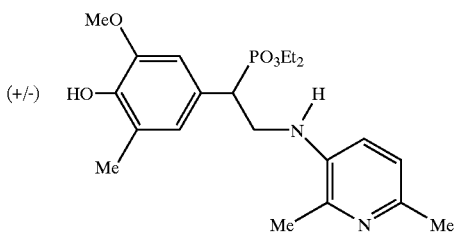

Method A:
The enantiomers of a racemic mixture (see Example 4) were separated by hplc using a chiral stationary phase (Chiracel OD) and hexane/ethanol (9/1) as the eluent. 0.615 g of the racemic mixture was processed to give 0.30 g of the faster eluting enantiomer as a foam ([α]$_D^{25}$ −58.4° (c=1.0 EtOH), optical purity=100%) and 0.27 g of the slower eluting enantiomer as a foam ([α]$_D^{25}$ +59.3° (c=1.0 EtOH), optical purity=100%).
Method B:
The enantiomers of a racemic mixture were separated by simulated moving bed chromatography using eight columns (100×26 mm i.d. each) packed with Chiracel OD and heptane/ethanol (7:3) as the eluent. 43 g of the racemic mixture was processed to give, after crystallisation from diethyl ether at −20° C., 15.5 g of the faster eluting enantiomer (mp=75.0–75.3° C., optical purity=99.6%) and 12.7 g of the slower eluting enantiomer (mp=69.5–71.0° C., optical purity=99.8%). The structures of both enantiomers were confirmed by NMR, IR and MS spectroscopies and elemental analyses.

Elemental analysis: C$_{21}$H$_{31}$N$_2$O$_5$P

| % Calc. | C 59.71 | H 7.40 | N 6.63 |
|---|---|---|---|
| (−)-enantiomer: | C 59.75 | H 7.46 | N 6.63 |
| (+)-enantiomer: | C 59.69 | H 7.39 | N 6.58 |

Example 12

Phosphate Salt of (−)-diethyl α-(4-hydroxy-3-methoxy-5-methylphenyl)-β-[N-(3-(2,6-dimethylpyridyl))-amino]-ethylphosphonate A solution of 85% phosphoric acid (0.136 g, 1.18 mmol) in water (0.7 ml) was added to a solution of (−)-diethyl α-(4-hydroxy-3-methoxy-5-methylphenyl)-β-[N-(3-(2,6-dimethylpyridyl))-amino]-ethylphosphonate (0.50 g, 1.18 mmol) in acetone (10 ml), after the addition a further 10 ml of acetone was added and the mixture stirred overnight. The resulting solid was collected by filtration, washed with acetone and dried under vacuum to give the title salt (0.344 g, 56%). [α]$_D^{25}$ −83.4° (c 1.0 H$_2$O), mp=167° C.

Example 13

Phosphate Salt of (+)-diethyl α-(4-hydroxy-3-methoxy-5-methylphenyl)-β-[N-(3-(2,6-dimethylpyridyl))-amino]-ethylphosphonate A solution of 85% phosphoric acid (1.366 g, 11.8 mmol) in water (7.0 ml) was added to a solution of (+)-diethyl α-(4-hydroxy-3-methoxy-5-methylphenyl)-β-[N-(3-(2,6-dimethylpyridyl))-amino]-ethylphosphonate (5.0 g, 11.8 mmol) in acetone (100 ml). After the addition a further 120 ml of acetone was added and the mixture stirred overnight at room temperature and then cooled in an ice bath for 5 h. The resulting solid was collected by filtration, washed with acetone and dried under vacuum to give the title salt (4.32 g, 70%). [α]$_D^{25}$ +85.2° (c=1.0 H$_2$O), mp=167.0–168.0° C., optical purity 99.4%.

Elemental analysis: C$_{21}$H$_{34}$N$_2$O$_9$P$_2$

| % Calc. | C 48.46 | H 6.58 | N 5.38 |
|---|---|---|---|
| Found | C 48.30 | H 6.33 | N 5.26 |

Example 14

Diethyl α-(4-hydroxy-3-methoxy-5-methylphenyl)-β-[N-(2-(5-methylpyrazinyl))-amino]-ethylphosphonate

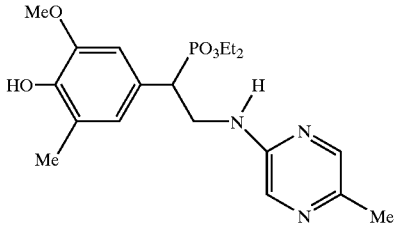

Step 1—(E)-diethyl α-(4-hydroxy-3-methoxy-5-methylphenyl)-β-[N-(2-(5-methylpyrazinyl))-amino]-vinylphosphonate:

A mixture of diethyl α-formyl (4-hydroxy-3-methoxy-5-methylbenzyl)phosphonate (1.45 g, 4.6 mmol) and 2-amino-5-methylpyrazine (0.50 g, 4.6 mmol) in 10 ml acetic acid was warmed to 40° C. for 4 h. The cooled solution was neutralized with a 20% NaOH solution, extracted with dichloromethane, dried over MgSO$_4$ and evaporated to give 1.84 g (99%) of a crude mixture containing mainly (E)-diethyl α-(4-hydroxy-3-methoxy-5-methylphenyl)-β-[N-(2-(5-methylpyrazinyl))-amino]-vinylphosphonate.

Physico-Chemical and Spectroscopic Data:

MS (m/e)=407: M$^+$, 270 (100%): M$^+$ —PO$_3$Et$_2$.

NMR (CDCl$_3$)=δ=8.12 (dd, J=13 and 16 Hz, 1H): (Ph)(P)C=CH—NH-pyrazine 8.04 and 8.0 (2 m, 2H total): aromatic H, pyrazine 6.86 (d, 1H, J=13 Hz): N—H 6.73 and 6.70 (2 s, 1H each): aromatic H, substituted phenyl 5.86 (s, 1H): OH 4.16–4.04 (m, 4H): P—O—CH$_2$—CH$_3$ 3.88 (s, 6H): Ph-OCH$_3$ 2.46 (s, 3H): pyrazine-CH$_3$ 2.27 (1 s, 3H): Ph-CH$_3$ 1.30 (t, J=7 Hz): P—O—CH$_2$—CH$_3$.

Step 2—Diethyl α-(4-hydroxy-3-methoxy-5-methylphenyl)-β-[N-(2-(5-methylpyrazinyl))-amino]-ethylphosphonate:

A solution of sodium cyanoborohydride (4.96 g, 79 mmol) and zinc chloride (5.38 g, 39 mmol) in 100 ml methanol was added to (E)-diethyl α-(4-hydroxy-3-methoxy-5-methylphenyl)-β-[N-(2-(5-methylpyrazinyl))-amino]-vinylphosphonate (1.34 g, 3.3 mmol) dissolved in 100 ml n-propanol and the turbid mixture was refluxed for 16 h. Methanol was distilled off at normal pressure to allow the reaction temperature to increase from ca 80° C. to 90° C. and the resulting mixture was refluxed for a further 16 h period. The mixture was partitioned between water and dichloromethane, the organic phase was dried and evaporated. Column chromatography (silica gel, 9/1 CH$_2$Cl$_2$/MeOH) gave 1.08 g (84%) of the title compound as a viscous oil which slowly solidified.

Physico-Chemical and Spectroscopic Data:

MS (m/e)=409: M$^+$, 288 (100%): M$^+$ —CH$_2$—NH—C$_5$H$_5$N$_2$.

NMR (CDCl$_3$): δ=7.86 (m, 1H) and 7.76 (d, 1H, J=1 Hz): aromatic H, pyrazine 6.74 and 6.68 (m, 2H): aromatic H, substituted phenyl 5.76 (s, 1H): OH 4.79 (t, 1H): N—H 4.15–3.75 (m, 4H): P—O—CH$_2$—CH$_3$ 4.15–4.03 and 3.85–3.70 (2 m, 2H): (Ph)(P)CH—CH$_2$—NH-pyrazine 3.85 (s, 3H): Ph-OCH$_3$ 3.36–3.28 (m, 1H): (Ph)(P)CH—CH$_2$—NH-pyrazine 2.37 (s, 3H): pyrazine-CH$_3$ 2.22 (s, 3H): Ph-CH$_3$ 1.32 and 1.15 (2 t, J=7 Hz): P—O—CH$_2$—CH$_3$.

Example 15

Diethyl α-(4-hydroxy-3-methoxy-5-methylphenyl)-β-[N-(2-pyrimidinyl)-amino]-ethylphosphonate

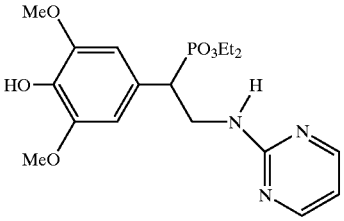

Step 1—(Z)- and (E)-diethyl α-(4-hydroxy-3-methoxy-5-methylphenyl)-β-[N-(2-pyrimidinyl)-amino]-vinylphosphonate:

A mixture of diethyl α-formyl (4-hydroxy-3-methoxy-5-methylbenzyl)phosphonate (1.0 g, 3.16 mmol) and 2-aminopyrimidine (0.30 g, 3.16 mmol) in 10 ml acetic acid was warmed to 40° C. for 4 h. The cooled solution was neutralized with a 20% NaOH solution, extracted with dichloromethane, dried over MgSO$_4$ and evaporated to give 1.21 g (97%) of a mixture of (Z)- and (E)-diethyl α-(4-hydroxy-3-methoxy-5-methylphenyl)-β-[N-(2-pyrimidinyl)-amino]-vinylphosphonate.

Physico-Chemical and Spectroscopic Data:

(Z)-Diethyl α-(4-hydroxy-3-methoxy-5-methylphenyl)-β-[N-(2-pyrimidinyl)-amino]-vinylphosphonate MS (m/e)=393: M$^+$, 256 (100%): M$^+$ —PO$_3$Et$_2$.

NMR (CDCl$_3$)=δ=10.48 (d, 1H, J=12 Hz): N—H 8.22 (dd, 1H, J=12 and 43 Hz): (Ph)(P)C=CH—NH-pyrimidine 8.44 (d, J=4.5 Hz, 2H) and 6.80 (t, J=4.5 Hz, 1H): aromatic H, 2-pyrimidinyl 6.85 and 6.81 (2 m, 2H): aromatic H, substituted phenyl 4.2–4.0 (m, 4H): P—O—CH$_2$—CH$_3$ 3.90 (s, 3H): Ph-OCH$_3$ 2.27 (is, 3H): Ph-CH$_3$ 1.31 (t, J=7 Hz): P—O—CH$_2$—CH$_3$.

(E)-Diethyl α-(4-hydroxy-3-methoxy-5-methylphenyl)-β-[N-(2-pyrimidinyl)-amino]-vinylphosphonate.

MS (m/e)=393: M$^+$, 256 (100%): M$^+$ —PO$_3$Et$_2$.

NMR (CDCl$_3$)=δ=8.42 (d, J=5 Hz, 2H) and 6.80 (t, J=5 Hz, 1H): aromatic H, 2-pyrimidinyl 8.33(dd, J=13 and 16 Hz, 1H): (Ph)(P)C=CH—NH-pyrimidine 7.41 (d, 1H, J=13 Hz): N—H 6.73 and 6.70 (2 m, 1H each): aromatic H, substituted phenyl 6.06 (s, 1H): OH 4.16–4.06 (m, 4H): P—O—CH$_2$—CH$_3$ 3.85 (s, 6H): Ph-OCH$_3$ 2.26 (is, 3H): Ph-CH$_3$ 1.32 (t, J=7 Hz): P—O—CH$_2$—CH$_3$.

Step 2—Diethyl α-(4-hydroxy-3-methoxy-5-methylphenyl)-β-[N-(2-pyrimidinyl)-amino]-ethylphosphonate:

A solution of sodium cyanoborohydride (0.38 g, 6 mmol, 8 eq) and zinc chloride (0.41 g, 3 mmol, 4 eq) in 40 ml methanol was added to the previous mixture of (Z)- and (E)-diethyl α-(4-hydroxy-3-methoxy-5-methylphenyl)-β-[N-(2-pyrimidinyl)-amino]-vinylphosphonate (0.3 g, 0.7 mmol) dissolved in 70 ml n-propanol and the turbid mixture was refluxed for 8 h. Three further portions of the same mixture of sodium cyanoborohydride (8 eq) and zinc chloride (4 eq) in MeOH were added every 8 h period of reflux to complete the conversion. The mixture was then partitioned between water and dichloromethane, the organic phase was dried and evaporated. Column chromatography (silica gel, 95/5 CH$_2$Cl$_2$/MeOH) gave 0.2 g (67%) of the title compound as a viscous oil which slowly solidified.

Physico-Chemical and Spectroscopic Data:

MS (m/e) 395: M$^+$, 288 (100%): M$^+$ —CH$_2$—NH—C$_4$H$_3$N$_2$.

NMR (CDCl$_3$): δ=8.27 (d, 2H, J=5 Hz) and 6.54 (t, 1H, J=3 Hz): aromatic H, 2-pyrimidine 6.76 and 6.72 (2 m, 2H): aromatic H, substituted phenyl 5.803 (s, 1H): OH 5.30 (t, 1H): N—H 4.15–3.94 (m, 4H): P—O—CH$_2$—CH$_3$ 4.24–4.16 (sextuplet, 1H) and 3.86–3.74 (m, 1H): (Ph)(P)CH—CH$_2$—NH-pyrimidine 3.86 (s, 3H): Ph-OCH$_3$ 3.43–3.33 (m, 1H): (Ph)(P)CH—CH$_2$—NH-pyrimidine 2.23 (is, 3H): Ph-CH$_3$ 1.33 and 1.17 (2 t, J=7 Hz): P—O—CH$_2$—CH$_3$.

Example 16

Diethyl α-(4-hydroxy-3-methoxy-5-methylphenyl)-β-[N-(3-(6-methylpyridazinyl))-amino]-ethylphosphonate

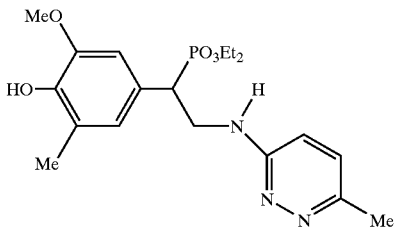

A mixture of diethyl α-formyl (4-hydroxy-3-methoxy-5-methylbenzyl)phosphonate (3.08 g, 9.15 mmol) and 3-amino-6-methylpyridazine (1.0 g, 9.16 mmol) in 20 ml acetic acid was warmed to 35° C. for 4 h. The cooled solution was neutralized with a 20% NaOH solution, extracted with dichloromethane, dried over MgSO$_4$ and evaporated to give 3.03 g (81%) of a mixture of (Z)- and (E)-diethyl α-(4-hydroxy-3-methoxy-5-methylphenyl)-β-[N-(3-(6-methylpyridazinyl))-amino]-vinylphosphonate.

A solution of sodium cyanoborohydride (9.84 g, 157 mmol) and zinc chloride (10.6 g, 78 mmol) in 290 ml methanol was added to a mixture of (Z) and (E)-diethyl α-(4-hydroxy-3methoxy-5-methylphenyl)-β-[N-(3-(6-methylpyridazinyl))-amino]-vinylphosphonate (2.66 g, 6.53 mmol) dissolved in 850 ml n-propanol and the turbid mixture was refluxed for 12 h. Methanol was distilled off at normal pressure to allow the reaction temperature to increase from ca 80° C. to 90° C. and the resulting mixture was refluxed for a further 12 h period. The mixture was partitioned between water and dichloromethane, the organic phase was dried and evaporated. Column chromatography (silica gel, 9/1 CH$_2$Cl$_2$/MeOH) gave 1.27 g (43%) of the title compound as a viscous oil which slowly solidified.
Physico-Chemical and Spectroscopic Data:
MS (m/e)=409: M$^+$, 288 (100%): M$^+$ —CH$_2$—NH—C$_5$H$_5$N$_2$.
NMR (CDCl$_3$): δ=7.0 and 6.53 (2 d, 1H each, J=9 Hz): aromatic H, pyridazine 6.74 and 6.718 (m, 2H): aromatic H, substituted phenyl 5.306 (s, 1H): OH 4.81 (t, 1H): N—H 4.1–3.8 (m, 4H): P—O—CH$_2$—CH$_3$ 4.15–4.05 and 3.90–3.80 (2 m, 2H): (Ph)(P)CH—CH$_2$—NH-pyridazine 3.84 (s, 3H): Ph-OCH$_3$ 3.36–3.28 (m, 1H): (Ph)(P)CH—CH$_2$—NH-pyridazine 2.51 (s, 3H): pyridazine-CH$_3$ 2.22 (s, 3H): Ph-CH$_3$ 1.30 and 1.14 (2 t, J=7 Hz): P—O—CH$_2$—CH$_3$.

Example 17

Diethyl α-(4-hydroxy-3-methoxy-5-methylphenyl)-β-[N-(5-(2,6-dimethylpyrimidinyl))-amino]-ethylphosphonate

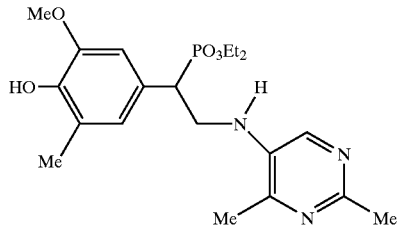

Step 1—(Z) and (E)-diethyl α-(4-hydroxy-3-methoxy-5-methylphenyl)-β-[N-(5-(2,6-dimethylpyrimidinyl))-amino]-vinylphosphonate:
A mixture of diethyl α-formyl (4-hydroxy-3-methoxy-5-methylbenzyl)phosphonate (2.5 g, 7.91 mmol) and 5-amino-2,6-dimethylpyrimidine (0.97 g, 7.91 mmol) in 20 ml acetic acid was warmed to 40° C. for 4 h. The cooled solution was neutralized first with a 20% NaOH then a saturated sodium bicarbonate solution, extracted with dichloromethane and the organic phase was dried over MgSO$_4$. The residue after evaporation was purified by column chromatography (silica gel, 95/5 CH$_2$Cl$_2$/MeOH) to give 1.8 g (54%) of a mixture of (Z) and (E)-diethyl α-(4-hydroxy-3-methoxy-5-methylphenyl)-β-[N-(5-(2,6-dimethylpyrimidinyl))-amino]-vinylphosphonate.
Physico-Chemical and Spectroscopic Data:
(Z)-diethyl α-(4-hydroxy-3-methoxy-5-methylphenyl)-β-[N-(5-(2,6-dimethylpyrimidinyl))-amino]-vinylphosphonate
MS (m/e)=421 (100%): M$^+$, 284: M+HPO$_3$Et$_2$.
NMR (CDCl$_3$)=δ=9.87 (d, 1H, J=13 Hz): N—H 826 (d, 1H): aromatic H, 5-pyrimidinyl 7.44 (dd, 1H, J=12 and 41 Hz): (Ph)(P)C=CH—NH-pyrimidine 6.78 and 6.72 (2 m, 2H): aromatic H, substituted phenyl ca 5.8 (broad, 1H): OH 4.18–4.02 (2 m, 4H): P—O—CH$_2$—CH$_3$ 3.88 (s, 3H): Ph-OCH$_3$ 2.64 and 2.53 (2 s, 6H total): Py-CH$_3$ 2.27 (1 s, 3H): Ph-CH$_3$ 1.31 (t, J=7 Hz): P—O—CH$_2$—CH$_3$.
(E)-diethyl α-(4-hydroxy-3-methoxy-5-methylphenyl)-β-[N-(5-(2,6-dimethylpyrimidinyl))-amino]-vinylphosphonate
MS (m/e)=421 (100%): M$^+$, 284: M$^+$ —HPO$_3$Et$_2$.
NMR (CDCl$_3$)=δ=7.61 (dd, 1H, J=13 and 15 Hz): (Ph)(P)C=CH—NH-pyrimidine 8.4 (s, 1H): aromatic H, 5-pyrimidinyl 6.76 and 6.74 (2m, 2H): aromatic H, substituted phenyl 6.24 (d, 1H, J=13 Hz): N—H 5.86 (broad, 1H): OH 4.16–4.04 (m, 4H): P—O—CH$_2$—CH$_3$ 3.89 (s, 3H): Ph-OCH$_3$ 2.63 and 2.26 (2 s, 6H total): Py-CH$_3$ 2.28 (1s, 3H): Ph-CH$_3$ 1.30 (t, J=7 Hz): P—O—CH$_2$—CH$_3$.
Step 2—Diethyl α-(4-hydroxy-3-methoxy-5-methylphenyl)-β-[N-(5-(2,6-dimethylpyrimidinyl))-amino]-ethylphosphonate:
A solution of sodium cyanoborohydride (1.17 g, 18.6 mmol) and zinc chloride (1.26 g, 9.26 mmol) in 50 ml methanol was added to a mixture of (Z) and (E)-diethyl α-(4-hydroxy-3-methoxy-5-methylphenyl)-1-[N-(5-(2,6-dimethylpyrimidinyl))-amino]-vinylphosphonate (1.30 g, 3.09 mmol) dissolved in 20 methanol and the mixture was refluxed for 16 h. The reaction mixture was partitioned between water and dichloromethane, the organic phase was dried and evaporated. Column chromatography (silica gel, 95/5 CH$_2$Cl$_2$/MeOH) gave 0.88 g (67%) of the title compound as a solid.

Physico-Chemical and Spectroscopic Data:

Melting point=172–174° C.

MS (m/e)=423: M+, 288: M+ —CH$_2$—NH—C$_6$H$_7$N$_2$.

NMR (CDCl$_3$): δ=7.92 (s, 1H): aromatic H, 5-pyrimidyl 6.74 and 6.67 (2 m, 2H): aromatic H, substituted phenyl 5.8 (s, 1H): OH 4.2–3.9 (m, 4H): P—O—CH$_2$—CH$_3$ 3.86 (s, 3H): Ph-OCH$_3$ 3.90–3.85 and 3.58–3.46 (2 m, 2H): (Ph)(P)CH—CH$_2$—NH-pyrimidine 3.31–3.22 (m, 1H): (Ph)(P)CH—CH$_2$—NH-pyrimidine 2.59 and 2.24 (2 s, 6H total): Pyrimidine-CH$_3$ 2.20 (1 s, 3): Ph-CH$_3$ 1.33 and 1.15 (2 t, J=7 Hz, 6H total): P—O—CH$_2$—CH$_3$.

Example 18

Diethyl α-(4-hydroxy-3-methoxy-5-methylphenyl)-β-[N-(2-thiazolyl)-amino]-ethylphosphonate

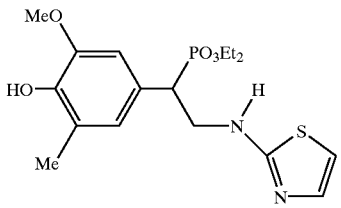

A mixture of diethyl α-formyl (4-hydroxy-3-methoxy-5-methylbenzyl)phosphonate (3.16 g, 10 mmol) and 2-aminothiazole (1.0 g, 10 mmol) in 20 ml acetic acid was warmed to 40° C. for 12 h. The cooled solution was neutralized with a 20% NaOH solution, extracted with dichloromethane, dried over MgSO$_4$ and evaporated to give 2.68 g (67%) of a mixture of (Z)- and (E)-diethyl α-(4-hydroxy-3-methoxy-5-methylphenyl)-J-[N-(2-thiazolyl)-amino]-vinylphosphonate.

A solution of sodium cyanoborohydride (0.90 g, 13.6 mmol, 4 eq) and zinc chloride (0.92 g, 6.8 mmol, 2 eq) in 20 ml methanol was added to the previous mixture of (Z)- and (E)-diethyl α-(4-hydroxy-3-methoxy-5-methylphenyl)-β-[N-(2-thiazolyl)-amino]-vinylphosphonate (1.35 g, 3.4 mmol) dissolved in 15 ml isopropanol and the turbid mixture was refluxed for 8 h. Another portion of the same mixture of sodium cyanoborohydride (4 eq) and zinc chloride (2 eq) in MeOH was to complete the conversion. After a total heating time of 72 h the mixture was then partitioned between water and dichloromethane, the organic phase was dried and evaporated. Column chromatography (silica gel, 95/5 AcOEt/MeOH) gave 0.4 g (31%) of the title compound as a viscous oil which slowly solidified.

Physico-Chemical and Spectroscopic Data:

MS (m/e)=400: M+, 288 (100%): M+ —CH$_2$—NH—C$_3$H$_2$NS

NMR (CDCl$_3$): δ=6.95 (m, 1H) and 6.45 (m, 1H): aromatic H, thiazole 6.76 and 6.72 (m, 2H): aromatic H, substituted phenyl 5.75 (s, 1H): OH 4.15–3.94 (m, 4H): P—O—CH$_2$—CH$_3$ 3.8–3.7 (m, 2H): (Ph)(P)CH—CH$_2$—NH-thiazole 3.86 (s, 3H): Ph-OCH$_3$ 3.40–3.30 (m, 1H): (Ph)(P)CH—CH$_2$—NH-thiazole 2.22 (is, 3H): Ph-CH$_3$ 1.33 and 1.15 (2 t, J=7 Hz): P—O—CH$_2$—CH$_3$.

Example 19

Diethyl α-(3-hydroxy-4-methoxyphenyl)-β-[N-(3-(2,6-dimethylpyridyl))-amino]-ethylphosphonate

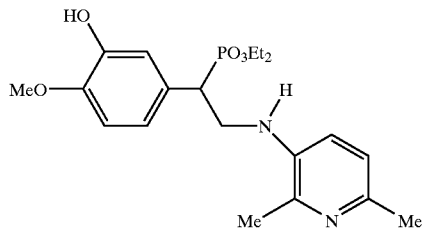

Potassium hydroxide (22.11 g, 0.39 mol) was added in one portion to a solution of dimethylamine hydrochloride (96.5 g, 1.18 mol) in 200 ml methanol. Isovanillin (30 g, 200 mol) was added and the resulting mixture was stirred at 20° C. for 30 min before a solution of sodium cyanoborohydride (24.87 g, 0.39 mol) in 100 ml methanol was added dropwise. After 30 min of stirring, potassium hydroxide (68.53 g, 1.22 mol) was added and stirring was continued until all the KOH pellets were dissolved. The reaction mixture was filtered, the filtrate was concentrated on a rotary evaporator and the concentrate was dissolved in water and acidified with 10% HCl to pH 3–4. After a prior extraction with diethyl ether which was discarded, the acidic aqueous phase was basified to pH ca 8 with a sodium carbonate solution and extracted with diethylther. The organic phase was dried over potassium carbonate and evaporated to dryness to give 32 g (88%) of a colorless oil.

To a dioxane solution (250 ml) of the dimethyl(3-hydroxy-4-methoxybenzyl)amine thus obtained (16 g, 88.5 mmol) was added methyl iodide (8.26 ml, 132 mmol) and the resulting mixture was refluxed for 4 h. The solid formed was filtered and washed with dioxane to yield 23 g (81%) of the trimethyl(3-hydroxy-4-methoxybenzyl) ammonium iodide salt. This latter was suspended in 100 ml xylene, triethyl phosphite (18 ml, 107 mmol) was added and the resulting mixture was refluxed for 16 h. The solid formed was filtered and the solvent and excess of phosphite were evaporated under vacuum to give after short path distillation diethyl (3-hydroxy-4-methoxybenzyl)phosphonate as a viscous oil (4 g, 10%).

A solution of n-butyl lithium (14.25 ml of a 2.5 M solution in hexanes, 37 mmol) was added over 5 min to a solution of diethyl (3-hydroxy-4-methoxybenzyl)phosphonate (3.9 g, 14 mmol) in THF (100 ml) which was cooled to −70° C. prior to reaction. The resulting suspension was stirred for a further 30 min at −70° C. then a solution of ethyl formate (23 ml, 285 mmol) in 20 ml THF was added and the mixture was stirred for a further 10 min. A saturated ammonium chloride solution was added and the reaction mixture was partitioned between diethyl ether and water. Evaporation of the dried ether phase (MgSO$_4$) and purification of the residue (silicagel, AcOEt) gave 1.7 g (40%) of a yellow oil.

A mixture of diethyl α-formyl (3-hydroxy-4-methoxybenzyl)phosphonate (1.7 g, 5.63 mmol) and 3-amino-2,6-dimethypyridine (0.69 g, 5.63 mmol) in 20 ml acetic acid was warmed to 40° C. for 4 h. The cooled solution was neutralized first with a 20% NaOH then a saturated sodium bicarbonate solution, extracted with dichloromethane and the organic phase was dried over MgSO$_4$. The residue after evaporation gave 2.10 g (92%) of a mixture of (Z) and (E)-diethyl α-(3-hydroxy-4- methoxyphenyl)-β-[N-(3-(2,6-dimethylpyridyl))-amino]-vinylphosphonate. This mixture was reduced by a solution of sodium cyanoborohydride 1.63 g, 25.9 mmol, 5 eq) and zinc chloride (2.11 g, 15.52 mmol, 3 eq) in methanol as described in Example 16 to give the title compound as a colorless oil (0.58 g, 30%).

Physico-Chemical and Spectroscopic Data:

MS (m/e)=408: M$^+$, 135 (100%)

NMR (CDCl$_3$): δ=6.94, 6.89 and 6.77 (3 m, 3H): aromatic H, substituted phenyl 6.83 and 6.81 (2 m, 2H): aromatic H, 3-pyridyl 6.3 (broad, 1H): N—H 5.3 (s, 1H): OH 4.15–3.80 (m, 4H): P—O—CH$_2$—CH$_3$ 3.88 (s, 3H): Ph-OCH$_3$ 3.86–3.81 and 3.56–3.48 (2 m, 2H): (Ph)(P)CH—CH$_2$—NH-pyridine 3.34–3.25 (m, 1H): (Ph)(P)CH—CH$_2$—NH-pyridine 2.41 and 2.18 (2 s, 6H total): Py-CH$_3$ 1.31 and 1.16 (2 t, J=7 Hz, 6H total): P—O—CH$_2$—CH$_3$.

Example 20

Diethyl α-(4-hydroxy-3-methoxy-5-methylphenyl)-β-[N-(2-benzothiazolyl)-amino]-ethylphosphonate

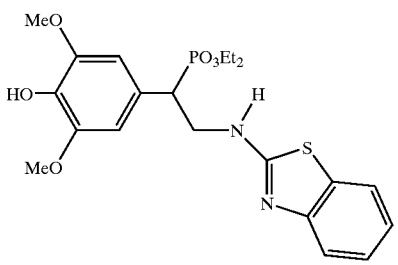

A mixture of diethyl α-formyl (4-hydroxy-3-methoxy-5-methylbenzyl)phosphonate (3.52 g, 11 mmol) and 2-aminobenzothiazole (1.67 g, 11 mmol and ca 5 mg of p-toluenesulfonic acid monohydryte in 20 ml ethanol was refluxed for 12 h.

A solution of sodium cyanoborohydride (1.45 g, 22 mmol, 2 eq) and zinc chloride (1.50 g, 11 mmol, 1 eq) in 30 ml methanol was added to the previous mixture and the resulting mixture was refluxed for 12 h. Another portion of the same mixture of sodium cyanoborohydride (2 eq) and zinc chloride (1 eq) in MeOH was added to complete the conversion. After a total heating time of 24 h the mixture was then partitioned between water and dichloromethane, the organic phase was dried and evaporated. Column chromatography (silica gel, 9/1 CH$_2$Cl$_2$/MeOH) gave 1.5 g (31%) of the title compound as a solid.

Physico-Chemical and Spectroscopic Data:

MS (m/e)=450: M$^+$, 288 (100%): M$^+$ —CH$_2$—NH—C$_7$H$_4$NS

NMR (CDCl$_3$): δ=7.57 (d, 1H), 752 (d, 1H), 7.28 (dt, 1H) and 7.08 (dt, 1H): aromatic H, benzothiazole 6.75 and 6.72 (m, 2H): aromatic H, substituted phenyl 5.30 (s, 1H): OH 4.18–3.94 (m, 4H): P—O—CH$_2$—CH$_3$ 4.18–4.06 and 3.96–3.82 (2 m, 2H): (Ph)(P)CH—CH$_2$—NH-benzothiazole 3.84 (s, 3H): Ph-OCH$_3$ 3.45–3.37 (m, 1H): (Ph)(P)CH—CH$_2$—NH-benzothiazole 2.23 (is, 3H): Ph-CH$_3$ 1.35 and 1.18 (2 t, J=7 Hz): P—O—CH$_2$—CH$_3$.

Example 21

Dimethyl α-(4-hydroxy-3-methoxy-5-methylphenyl)-β-[N-(3-(2,6-dimethylpyridyl))-amino]-ethylphosphonate

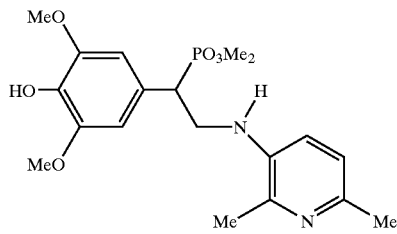

Trimethyl(4-hydroxy-3-methoxy-5-methylbenzyl) ammonium iodide (1 g, 3.0 mmol) was suspended in 8 ml xylene, trimethyl phosphite (0.52 ml, 4.4 mmol) was added dropwise and the resulting mixture was refluxed for 14 h. The solid formed was filtered and the solvent and excess of phosphite were evaporated under vacuum to yield dimethyl (4-hydroxy-3-methoxy-5-methylbenzyl)phosphonate as a viscous oil (0.64 g, 83%).

A solution of the above compound (0.87 g, 3.34 mmol) in THF (24 ml) was cooled to −70° C. A solution of n-butyl lithium (6.3 ml of 1.6 M solution in n-hexane, 10.1 mmol) was added drowise. The resulting thick suspension was stirred for a further 30 min at −70° C. A solution of ethyl formate (1.5 ml, 18.3 mmol) in THF (3 ml) was added dropwise and the mixture stirred for a further 10 min at −70° C., then saturated aqueous ammonium chloride (25 ml) was added and the mixture allowed to warm to room temperature. Diethyl ether and water were added, the organic phase was washed with brine, then dried over MgSO$_4$ The residue of the evaporated extract gave 1.02 g (96%, crude) of dimethyl α-formyl (4-hydroxy-3-methoxy-5-methylbenzyl) phosphonate as a brown oil.

A mixture of the above compound (0.51 g, 1.7 mmol) and 3-amino-2,6-dimethylpyridine (0.18 g, 1.43 mmol) in 3 ml acetic acid was warmed to 40° C. for 4 h. The cooled solution was neutralized first with a 20% NaOH then a saturated sodium bicarbonate solution, extracted with dichloromethane and the organic phase was dried over MgSO$_4$. The residue after evaporation gave 0.65 g (100%) of a mixture of (Z)- and (E)-dimethyl α-(4-hydroxy-3-methoxy-5-methylphenyl)-β-[N-(3-(2,6-dimethylpyridyl))-amino]-vinylphosphonate 10% Palladium on activated charcoal (0.35 g) was added to a the above mixture dissolved in 14 ml acetic acid and the mixture was submitted to hydrogenation under atmospheric pressure in a Parr apparatus for 24 h at room temperature. The mixture was neutralized with a 10% sodium hydroxide solution, extracted with dichloromethane, dried and evaporated. Column chromatography (silica gel, 9/1 CH$_2$Cl$_2$/MeOH) gave 0.44 g (67%) of the title compound as a viscous oil which slowly solidified.

Physico-Chemical and Spectroscopic Data:

MS (m/e)=394: M$^+$, 260: M$^+$ —CH$_2$—NH—C$_7$H$_8$N, 135 (100%)

NMR (CDCl$_3$): δ=6.90 and 6.83 (2 d, J=9 Hz, 2H): aromatic H, 3-pyridyl 6.73 and 6.68 (2 m, 2H): aromatic H, substituted phenyl 5.7 (broad, 1H): OH 3.85 (s, 3H): Ph-OCH$_3$ 3.75 and 3.55 (2 d, 7 Hz, 6H): P—O—CH$_3$ ca 3.8 and 3.5 (2 m, 2H): (Ph)(P)CH—CH$_2$—NH-pyridine 3.3 (m, 1H): (Ph)(P)CH—CH$_2$—NH-pyridine 2.42 and 2.23 (2 s, 6H total): Py-CH$_3$ 2.18 (1 s, 3H): Ph-CH$_3$ 1.33 and 1.15 (2 t, J=7 Hz, 6H total): P—O—CH$_2$—CH$_3$.

Example 22

Diethyl α-phenyl-β-[N-(3-(2,6-dimethylpyridyl))-amino]-ethylphosphonate

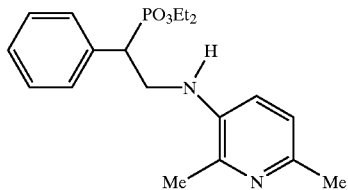

A solution of n-butyl lithium (112 ml of a 1.6 M solution in hexanes, 179 mmol) was added over 15 min to a solution of diethyl benzylphosphonate (25 g, 110 mmol) in THF (625 ml) which was cooled to −70° C. prior to reaction. The resulting suspension was stirred for a further 30 min at −70° C. then a solution of ethyl formate (31 ml, 440 mmol) in 62 ml THF was added and the mixture was stirred for a further 10 min. A saturated ammonium chloride solution was added and the reaction mixture was partitioned between diethyl ether and water. Evaporation of the dried ether phase (MgSO$_4$)) gave 26.6 g (95%, crude yield) of an yellow oil.

A mixture of diethyl α-formyl benzylphosphonate (26.6 g, 103 mmol) and 3-amino-2,6-dimethypyridine (11 g, 90 mmol) in 20 ml acetic acid was warmed to 40° C. for 4 h. The cooled solution was neutralized first with a 20% NaOH then a saturated sodium bicarbonate solution, extracted with dichloromethane and the organic phase was dried over MgSO$_4$. The residue after evaporation gave 27 g (83%) of a mixture of (Z) and (E)-diethyl α-phenyl-β-[N-(3-(2,6-dimethylpyridyl))-amino]-vinylphosphonate. This mixture was catalytically reduced by 10% Palladium over charcoal (6 g) in acetic acid as previously described to give the title compound as a colorless oil (19 g, 70%) which slowly solidified after column chromatography (SiO$_2$, 98/2 CHCl$_3$/MeOH).

Physico-Chemical and Spectroscopic Data:

MS (m/e)=362: M$^+$, 228, 135 (100%)

NMR (CDCl$_3$): δ=7.84 (m, 5H): aromatic H, substituted phenyl 6.92 and 6.84 (2 m, 2H): aromatic H, 3-pyridyl 4.1, 3.95 and 3.90 (3 m, 4H): P—O—C$\underline{H}_2$—CH$_3$ 3.8 (m, 1H): (Ph)(P)C$\underline{H}$—CH$_2$—NH-pyridine 3.5 and 3.4 (2 m, 2H): (Ph)(P)CH—C$\underline{H}_2$—NH-pyridine 2.43 and 2.18 (2 s, 6H total): Py-C$\underline{H}_3$ 1.31 and 1.12 (2 t, J=7 Hz, 6H total): P—O—CH$_2$—C$\underline{H}_3$.

Example 23

Diethyl α-(4-hydroxy-3-methoxy-5-methylphenyl)-β-[N-methyl-N-(3-picolyl)-amino]-ethylphosphonate

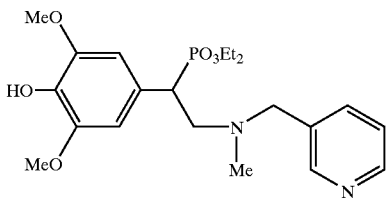

A mixture of diethyl α-formyl (4-hydroxy-3-methoxy-5-methylbenzyl)phosphonate (2.93 g, 9.3 mmol), N-methyl-3-picolylamine (1.0 g, 9.3 mmol) and ca 5 ml acetic acid in 50 ml ethanol was heated to reflux for 3 h. The reaction mixture was cooled to room temperature, sodium cyanoborohydride (1.75 g, 28 mmol) was added and the resulting mixture was heated to 60° C. for 1 h. The cooled solution was partitioned between 50 ml water and 100 ml dichloromethane, the organic phase was dried over MgSO$_4$. Purification by column chromatography (SiO$_2$, 9/1 AcOEt/MeOH) gave ca 3.0 g (76%) of the title compound.

Physico-Chemical and Spectroscopic Data:

MS (m/e)=422: M$^+$, 135 (100%, 3-Py-CH$_2$—N(Me)—CH$_2$), 92 (3-Py-CH$_2$)

NMR (CDCl$_3$): δ=8.45, 8.38, 7.41 and 7.14 (4 m, 1H each): aromatic H, 3-picolyl 6.63 and 6.61 (2 m, 2H): aromatic H, substituted phenyl, 5.72 (s, 11H): O$\underline{H}$ 4.05 and 3.86 (m, 4H): P—O—C$\underline{H}_2$—CH$_3$ 3.82 (s, 3H): Ph-OC$\underline{H}_3$ 3.65 and 3.0 (2 m, 2H): (Ph)P—CH—C$\underline{H}_2$—N(Me)—CH$_2$—Py 3.60 and 3.48 (2 d, 1H): N(Me)—C$\underline{H}_2$—Py 3.2 (m, 1H): (Ph)(P)C$\underline{H}$—CH$_2$—N(Me)—CH$_2$—Py 2.23 and 2.21 (2 s, 3H each): N—C$\underline{H}_3$ and Ph-C$\underline{H}_3$ 1.29 and 1.08 (2 t, J=7 Hz): P—O—CH$_2$—C$\underline{H}_3$.

Example 24

Diethyl α-methyl-α-(4-hydroxy-3-methoxy-5-methylphenyl)-β-[N-(3-(2,6-dimethylpyridyl))-amino]-ethylphosphonate

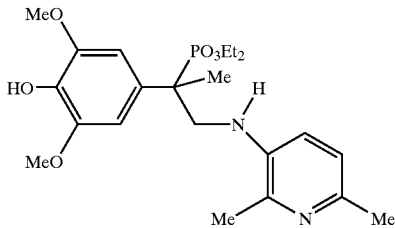

Step 1—Diethyl α-(4-t-butyldimethylsilyloxy-3-methoxy-5-methyl) Benzylphosphonate:

Imidazole (7.08 g, 104 mmol) was added portionwise to a well stirred mixture of diethyl (4-hydroxy-3-methoxy-5-methylbenzyl)phosphonate (10 g, 35 mmol) and t-butyldimethylsilyl chloride (7.84 g, 52 mmol) in 25 ml DMF and stirring was continued for 16 h at room temperature. The mixture was poured into water kept at 0° C. to which was added a 25% ammonium hydroxide solution until pH 7 was reached. The aqueous phase was extracted with chloroform, the organic phase was dried over MgSO$_4$. Evaporation of the solvent gave 14 g (100%) of diethyl (4-t-butyldimethylsilyloxy-3-methoxy-5-methylbenzyl)phosphonate as a dark oil.

Step 2—Diethyl α-methyl-α-(4-t-butyldimethylsilyloxy-3-methoxy-5-methyl) Benzylphosphonate:

Under a nitrogen atmosphere n-butyllithium (12 ml of a 1.6 M solution in hexane, 18.6 mmol) was added dropwise to a solution of diethyl (4-t-butyldimethylsilyloxy-3-methoxy-5-methylbenzyl)phosphonate (3 g, 7.5 mmol) in 10 ml dry THF kept at −78° C. The resulting mixture was stirred at −78° C. for 30 min then a solution of methyl iodide (1.2 ml, 18.6 mmol) in 5 ml THF was added dropwise. The reaction temperature was left to reach room temperature and stirred overnight then hydrolysis was carried out with a saturated ammonium chloride solution. The quenched reaction mixture was extracted with diethyl ether, the ether extract was dried over MgSO$_4$, filtered and evaporated to dryness to yield as an oil. GC analysis indicated a mixture of the sub-title compound (ca 42%) and diethyl α,α-dimethyl-(4-t-butyldimethylsilyloxy-3-methoxy-5- methylbenzyl)phosphonate (ca 38%); the starting compound has completely reacted.

Step 3—Diethyl α-methyl-α-(4-t-butyldimethylsilyloxy-3-methoxy-5-methyl)-α-formyl Benzylphosphonate:

Under a nitrogen atmosphere n-butyllithium (17 ml of a 1.6 M solution in hexane, 27.3 mmol) was added dropwise to a solution of diethyl α-methyl-(4-t-butyldimethylsilyloxy-3-methoxy-5-methylbenzyl) phosphonate (3.8 g of a 42% mixture, 3.8 mmol) in 30 ml dry THF cooled to −78° C. After 15 min stirring at −78° C. ethyl formate (2.1 g, 27.3 mmol) was added, the resulting mixture was stirred at −78° C. for 15 min then hydrolysis was carried out by adding a saturated ammonium chloride solution. The quenched reaction mixture was extracted with chloroform, the organic extract was dried over MgSO$_4$, filtered and evaporated to dryness to yield the subtitle compound as a red oil which was directly used for the next step (3.5 g, ca 50% pure by GC).

Step 4—α-(Diethyl Phosphonyl)-α-methyl-(4-t-butyldimethylsilyloxy-3-methoxy-5-methyl)phenylacetaldehyde)[-3-(2,6-dimethylpyridine]imine:

A mixture of diethyl α-methyl-α-(4-t-butyldimethylsilyloxy-3-methoxy-5-methyl)-α-formyl benzylphosphonate (3.5 g) and 3-amino-2,6-dimethylpyridine (0.39 g, 32 mmol) in 30 ml toluene and a catalytic amount of p-toluenesulfonic acid was refluxed for 16 h in a Dean-Stark apparatus. The cooled solution was evaporated to dryness to yield a red oil which was used directly for the next step.

Step 5—Diethyl α-methyl-α-(4-t-butyldimethylsilyloxy-3-methoxy-5-methyl)-β-[N-3-(2,6-dimethylpyridyl))amino]-ethylphosphonate:

Sodium borohydride (0.54 g, 14 mmol) was added portionwise to the compound from the previous step (3.9 g, 7 mmol) dissolved in 30 ml EtOH and the resulting mixture was refluxed for 3 h. Ethanol was evaporated and the residue was partitioned between water and chloroform, the organic phase died, evaporated and the residue was purified by column chromatography (silica gel, 95/5 CHCl$_3$/MeOH). The title compound was obtained as an oil (1.7 g, 44%).

Step 6—Diethyl α-methyl-α-(4-hydroxy-3-methoxy-5-methyl)-β-[N-3-(2,6-dimethylpyridyl))amino]-ethylphosphonate:

The previous compound (1.7 g, 3.1 mmol) and TBAF (3.9 g, 12.4 mmol) were placed in 20 ml THF to which glacial acetic acid (0.74 g, 12.4 mmol) was added dropwise. After stirring at 20° C. for 4 h the reaction mixture was partitioned between water and chloroform, the organic phase was washed with a saturated bicarbonate solution, dried over MgSO$_4$. The residue of the evaporated extract was purified by column chromatography (silica gel, 95/5 CHCl$_3$/MeOH). The pure fractions gave 0.8 g (59%) of the title compound.

Physico-Chemical and Spectroscopic Data:

MS (m/e)=436: M$^+$, 302: M$^+$ —CH$_2$—NH—C$_7$H$_9$N, 135 (100%)

NMR (CDCl$_3$): δ=7.07 and 6.92 (2 m, 2H): aromatic H, substituted phenyl 6.88 and 6.82 (2 d, J=8 Hz, 2H): aromatic H, 3-pyridyl 5.7 (broad, 1H): N—H 4.1–3.9 (m, 4H): P—O—CH$_2$—CH$_3$ 3.86 (s, 3H): Ph-OCH$_3$ 3.85–3.77 and 3.66–3.56 (2 m, 2H): (Ph)(P)C—CH$_3$—CH$_2$—NH-pyridine 2.42 and 2.26 (2 s, 6H total): Py-CH$_3$ 2.24 (1 s, 3H): Ph-CH$_3$ 1.7 (d, J=16 Hz, 3H): (Ph)(P)C—CH$_3$—CH$_2$—NH-pyridine 1.29 and 1.18 (2 t, J=7 Hz, 6H total): P—O—CH$_2$—CH$_3$.

Example 25

Diethyl α-(3,5-dimethyl-4-hydroxyphenyl)-β-[N-(pyrazinyl)-amino]-ethylphosphonate

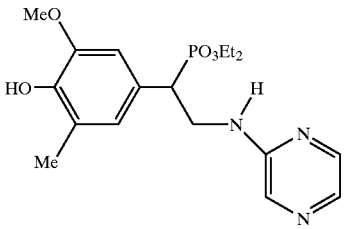

The title compound was prepared as described in example 6, using (Z)-/(E)-diethyl α-(3,5-dimethyl-4-hydroxyphenyl)-β-[N-(pyrazinyl)-amino]-vinylphosphonate as the starting compound.

Spectroscopic Data:

MS (m/e)=379: M$^+$, 272 (100%): M$^+$ —CH$_2$—NH—C$_4$H$_3$N$_2$.

NMR (CDCl$_3$): δ=7.97 (m, 1H), 7.83 (m, 1H) and 7.78 (d, 1H, J=3 Hz): aromatic H, pyrazine 6.92 (d, 2H): aromatic H, substituted phenyl 5.73 (s, 1H): OH 5.05 (t, J=6 Hz, 1H): N—H 4.15–3.75 (3 m, 6H): P—O—CH$_2$—CH$_3$ and (Ph)(P)CH—CH$_2$—NH-pyrazine 3.34–3.30 (m, 1H): (Ph)(P)CH—CH$_2$—NH-pyrazine 2.19 and 2.18 (2 s, 6H): Ph-CH$_3$ 1.30 and 1.17 (2 t, J=7 Hz): P—O—CH$_2$—CH$_3$.

Example 26

Diethyl α-(3-tert-butyl-4-hydroxy-5-methylphenyl)-β-[N-(pyrazinyl)-amino]-ethylphosphonate

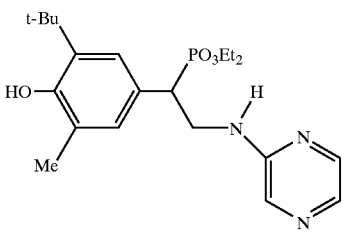

The title compound was prepared as described in example 6, using (Z)-/(E)-diethyl α-(3-tert-butyl-4-hydroxy-5-methylphenyl)-β-[N-(pyrazinyl)-amino]-vinylphosphonate as the starting compound.

Spectroscopic Data:

MS (m/e)=421: M$^+$, 314 (100%): M$^+$ —CH$_2$—NH—C$_4$H$_3$N$_2$.

NMR (CDCl$_3$): δ=7.98 (m, 1H), 7.83 (m, 1H) and 7.79 (d, 1H, J=3 Hz): aromatic H, pyrazine 7.14 and 7.04 (2 m, 2H): aromatic H, substituted phenyl 5.15 (s, 1H): OH 5.07 (t, J=6 Hz, 1H): N—H 4.15–3.75 (3 m, 6H): P—O—CH$_2$—CH$_3$ and (Ph)(P)CH—CH$_2$—NH-pyrazine 3.39–3.31 (m, 1H): (Ph)(P)CH—CH$_2$—NH-pyrazine 2.17 (s, 3H): Ph-CH$_3$ 1.38 (s, 3H): t-C$_4$H$_9$ 1.31 and 1.14 (2 t, J=7 Hz): P—O—CH$_2$—CH$_3$.

Example 27

Diethyl α-methyl-α-(4-hydroxy-3-methoxy-5-methylphenyl)-β-[N-pyrazinyl)-amino]-ethylphosphonate

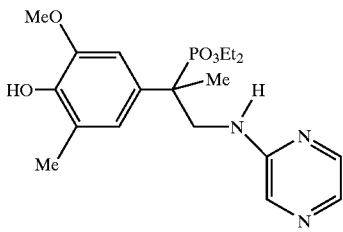

The title compound was prepared according to the procedure described in Example 24, using aminopyrazine as the amine.

Spectroscopic Data:
MS (m/e)=409: M$^+$, 302: M$^+$ —CH$_2$—NH—C$_4$H$_3$N$_2$ (100%)
NMR (DMSO-d$_6$): δ=8.40 (s, 1H): OH, 7.92 and 7.61 (2 m, 3H): aromatic H, pyrazine, 6.88 and 6.77 (2 m, 2H): aromatic H, substituted phenyl, 6.57 (t, J=6 Hz, 11H): N—H 3.90–3.65 (several m, 6H): P—O—C$\underline{H}_2$—CH$_3$ and (Ph)(P) C—CH$_3$—C$\underline{H}_2$—NH-pyridazine 3.70 (s, 3H): Ph-OC$\underline{H}_3$ 2.42 and 2.26 (2 s, 6H total): Py-C$\underline{H}_3$ 2.1 (1 s, 3H): Ph-C$\underline{H}_3$ 1.54 (d, J=16 Hz, 3H): (Ph)(P)C—C$\underline{H}_3$—CH$_2$—NH-pyridazine 1.18 and 1.10 (2 t, J=7 Hz, 6H total): P—O—CH$_2$—C$\underline{H}_3$.

Example 28

Diethyl α-(4-hydroxy-3-methoxy-5-methylphenyl)-β-[N-(3-(2,6-dimethyl)-aminopyridyl]-propylphosphonate

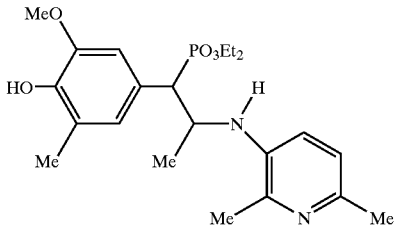

Step 1: Diethyl α-acetyl (4-tert-butyl-dimethylsilyloxy-3-methoxy-5-methyl)-benzylphosphonate.

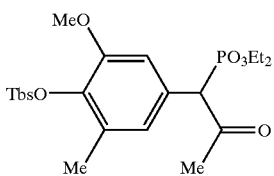

Diethyl (4-tert-butyl-dimethylsilyloxy-3-methoxy-5-methyl)-benzylphosphonate (176 g, 0.43 mol) was prepared by reacting diethyl (4-hydroxy-3-methoxy-5-methyl)-benzylphosphonate (130 g, 0.43 mol) with tert-butyl-dimethylsilyl chloride (96.5 g, 0.64 mol) in 400 ml of DMF in presence of imidazole (58.2 g, 0.86 mol).

A solution of diethyl (4-tert-butyl-dimethylsilyloxy-3-methoxy-5-methyl)-benzylphosphonate (20 g, 49.7 mmol) in 25 ml THF was added dropwise to a solution of nBuLi 1.6M (51.5 ml, 82 mmol) and diisopropylamine (11.8 ml, 83 mmol) in 50 ml THF kept at −78° C. After 30 min, a solution of ethyl acetate (5.35 ml, 54.6 mmol) in 10 ml THF was added dropwise and stirring was continued for 15 min. Next water was added, followed by 20 ml of saturated NH$_4$Cl. The product was extracted with CHCl$_3$, washed with brine and dried on MgSO$_4$. Evaporation gave 23.5 g of a brown oil which yielded after column chromatography (98/2 AcOEt/MeOH) 10.2 g(22.98 mmol, 46%) of the title compound.

Step 2: Diethyl α-(4-tert-butyl-dimethylsilyloxy-3-methoxy-5-methylphenyl)-β-[N-(3-(2,6-dimethyl)-aminopyridyl]-propylphosphonate:

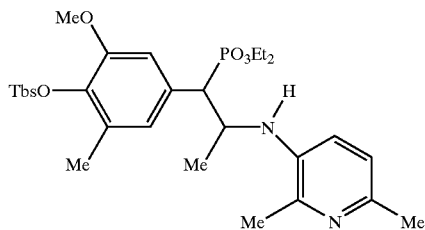

A mixture of diethyl (x-acetyl (4-tert-butyl-dimethylsilyloxy-3-methoxy-5-methyl)-benzylphosphonate (1.0 g, 2.2 mmol) and 3-amino-2,6-dimethylpyridine (0.28 g, 2.2 mmol) in 20 ml xylene was refluxed for 3 hours. The mixture was evaporated to dryness and the residue dissolved in 10 ml ethyl alcohol. Then a solution of sodium cyanohydride (0.90 g, 6.6 mmol) and zinc chloride (0.83 g, 13.2 mmol) in 20 ml methanol was added. The resulting mixture was stirred overnight at room temperature. Methanol was evaporated and the residue partitioned between water and chloroform. The organic phase was evaporated to give 1.46 g of a brown oil. Purification by column chromatography (95/5 CHCl$_3$/MeOH) yielded 0.90 g (1.64 mmol, 74%) of the title compound.

Step 3: Deprotection

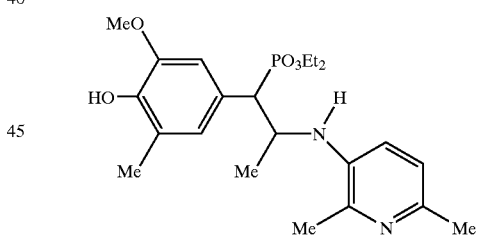

A solution of tetrabutylammonium fluoride (2.06 g, 6.5 mmol) in 40 ml THF was added in one portion to a solution of the preceding compound (0.9 g, 1.64 mmol) in 40 ml THF. The resulting solution was stirred at room temperature for 3 h then was partitioned between water and chloroform. The organic phase was separated, dried over MgSO$_4$ and evaporated to give 0.7 g of a brown oil. Purification by column chromatography (95/5 CHCl$_3$/MeOH) gave 0.09 g (0.21 mmol, 13%) of the first (earlier eluting) diastereomer as a crystallizing oil, 0.25 g (0.57 mmol, 35%) of a mixture of the earlier and later eluting diastereomers and 0.16 g (0.36 mmol, 22%) of the second (later eluting) diastereomer).

Spectroscopic Data of First Eluting Diastereomer:
MS (m/e)=436: M$^+$, 149(100%): M$^+$ —CH(CH$_3$)—NH—(2,6-dimethyl-3-pyridyl)
NMR (CDCl$_3$): δ=6.93 and 6.90 (2 d, 1H each, J=8.2 Hz): aromatic H, pyridine 6.76 and 6.53 (2 s, 1H each): aromatic H, substituted phenyl 5.70 (s, 1H): NH 4.20–3.70 (m, 4H): P—OC$\underline{H}_2$—CH$_3$ masked in 4.20–3.70: β-CH 3.81 (s, 3H): Ph-OC$\underline{H}_3$ 3.29 (dxd, 1H): α-CH 2.44 and 2.29 (2 s, 6H): 2,6-dimethyl-3-pyridyl 2.21 (s, 3H): Ph-C$\underline{H}_3$ 1.36 and 1.09 (2 t, 6H): P—OCH$_2$—C$\underline{H}_3$ 1.30 (d, 3H, J=6.5 Hz): β-CH$_3$.

Spectroscopic Data of Second Eluting Diastereomer:

MS (m/e)=436:M$^+$, 149(100%): M$^+$ —CH(CH$_3$)—NH—(2,6-dimethyl-3-pyridyl)

NMR (CDCl$_3$): δ=6.90 and 6.71 (2 s, 1H each): aromatic H, substituted phenyl 6.89 and 6.84 (2 d, 1H each, J=8.2 Hz): aromatic H, pyridine 5.71 (s, 1H): NH 4.12–3.69 (m, 4H): P—OC$\underline{H}_2$—CH$_3$ masked in 4.12–3.90: β-CH 3.84 (s, 3H): Ph-OC$\underline{H}_3$ 3.18 (dxd, 1H, J=23.4 and 4.4 Hz): α-CH 2.41 and 2.28 (2 s, 6H): 2,6-dimethyl-3-pyridyl 2.25 (s, 3H): Ph-C$\underline{H}_3$ 1.38 (d, 3H, J=6.1 Hz): P—C$\underline{H}_3$ 1.29 and 1.10 (2 t, 6H): P—OCH$_2$—C$\underline{H}_3$.

Example 29

Summary of Synthesized Compounds

Summarized in TABLE 1 are aminophosphonates of formula (Ia) where $Z^0, X^1, X^5, Y^1, Y^2$ and $Y^3$ are H, m=0 and n=0, designated as (Ia') and aminophosphonates of formula (Ib) where $Z^0, X^1, X^5, Y^3$ are H, m=0 and n=0, designated as (Ib'), wherein the compounds of formulas (Ia') and (Ib') were prepared according to the processes hereinbefore described:

TABLE 1

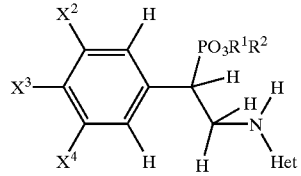
(Ia')

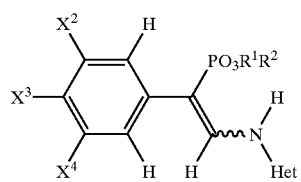
(Ib')

| Cpd | $X^2$ | $X^3$ | $X^4$ | Formula (isomer) | Het | $R^1, R^2$ | mp (° C.) |
|---|---|---|---|---|---|---|---|
| 1 | OMe | OH | OMe | (Ib') (Z) | 3-pyridyl | Et | 173–174 |
| 2 | OMe | OH | Me | (Ib') (Z) | 3-pyridyl | Et | 128–130 |
| 3 | OMe | OH | Me | (Ib') (Z) | 3-pyridyl | iPr | Solid |
| 4 | OMe | OH | OMe | (Ib') (Z) | 3-(2,6-dimethyl-pyridyl) | Et | 165–167 |
| 5 | OMe | OH | Me | (Ib') (Z) | 3-(2,6-dimethyl-pyridyl) | Et | 136–138 |
| 6 | OMe | OH | OMe | (Ib') (Z) | pyrazinyl | Et | 138–140 |
| 7 | OMe | OH | OMe | (Ib') (Z) | pyrazinyl | iPr | 168–170 |
| 8 | OMe | OH | Me | (Ib') (Z) | pyrazinyl | Et | 136–138 |
| 9 | OMe | OH | OMe | (Ib') (Z) | 2-pyrimidinyl | Et | 119–121 |
| 10 | OMe | OH | OMe | (Ib') (Z) | 2-pyrimidinyl | iPr | 121–122 |
| 11 | OMe | OH | Me | (Ib') (Z) | 2-pyrimidinyl | Et | 110–112 |
| 12 | Me | OH | Me | (Ib') (Z) | 3-(2,6-dimethyl-pyridyl) | iPr | 122–124 |
| 13 | OMe | OH | OMe | (Ib') (E) | 3-pyridyl | Et | 201–203 |
| 14 | OMe | OH | OMe | (Ib') (E) | 3-pyridyl | iPr | 184–187 |
| 15 | OMe | OH | Me | (Ib') (E) | 3-pyridyl | Et | Solid |
| 16 | OMe | OH | Me | (Ib') (E) | 3-pyridyl | iPr | 138–140 |
| 17 | OMe | OH | OMe | (Ib') (E) | 3-(2,6-dimethyl-pyridyl) | iPr | 110–112 |
| 18 | OMe | OH | Me | (Ib') (E) | 3-(2,6-dimethyl-pyridyl) | Et | 136–138 |
| 19 | OMe | OH | Me | (Ib') (E) | 3-(2,6-dimethyl-pyridyl) | iPr | 140–142 |
| 20 | OMe | OH | Me | (Ib') (E) | 5-(2-methyl-pyridyl) | Et | 151–153 |
| 21 | OMe | OH | Me | (Ib') (E) | 5-(2-methyloxy-pyridyl) | Et | wax |
| 22 | OMe | OH | OMe | (Ib') (E) | pyrazinyl | iPr | 189–191 |
| 23 | OMe | OH | Me | (Ib') (E) | pyrazinyl | Et | Solid |
| 24 | OMe | OH | OMe | (Ib') (E) | 2-pyrimidinyl | Et | Solid |
| 25 | OMe | OH | OMe | (Ib') (E) | 2-pyrimidinyl | iPr | 168–170 |
| 26 | OMe | OH | Me | (Ib') (E) | 2-pyrimidinyl | Et | 168–170 |
| 27 | Me | OH | Me | (Ib') (E) | 3-pyridyl | Et | 193–195 |
| 28 | Me | OH | Me | (Ib') (E) | 3-pyridyl | iPr | 192–194 |
| 29 | Me | OH | Me | (Ib') (E) | 3-(2,6-dimethyl-pyridyl) | Et | 154–156 |
| 30 | Me | OH | Me | (Ib') (E) | 5-(2-methyl-pyridyl) | Et | 210–212 |
| 31 | Me | OH | Me | (Ib') (E) | 5-(2-methyl-pyridyl) | iPr | 211–213 |
| 32 | OMe | OH | OMe | (Ia') | 3-pyridyl | Et | 152–154 |
| 33 | OMe | OH | OMe | (Ia') | 3-pyridyl | iPr | 156–158 |
| 34 | OMe | OH | Me | (Ia') | 3-pyridyl | Et | Solid |
| 35 | OMe | OH | Me | (Ia') | 3-pyridyl | iPr | Solid |
| 36 | OMe | OH | OMe | (Ia') | 3-(2,6-dimethyl-pyridyl) | Et | Solid |
| 37 | OMe | OH | OMe | (Ia') | 3-(2,6-dimethyl-pyridyl) | iPr | 165–167 |
| 38 | OMe | OH | Me | (Ia') | 3-(2,6-dimethyl-pyridyl) | Et | 82–85 |
| 39 | OMe | OH | Me | (Ia') | 3-(2,6-dimethyl-pyridyl) | iPr | 128–130 |
| 40 | OMe | OH | Me | (Ia') | 5-(2-methyl-pyridyl) | Et | Solid |
| 41 | OMe | OH | Me | (Ia') | 5-(2-methyloxy-pyridyl) | Et | Wax |
| 42 | OMe | OH | OMe | (Ia') | pyrazinyl | Et | 147–148 |
| 43 | OMe | OH | OMe | (Ia') | pyrazinyl | iPr | 169–171 |
| 44 | OMe | OH | Me | (Ia') | pyrazinyl | Et | 160–164 |
| 45 | OMe | OH | OMe | (Ia') | 2-pyrimidinyl | iPr | wax |
| 46 | Me | OH | Me | (Ia') | 3-pyridyl | Et | Solid |
| 47 | Me | OH | Me | (Ia') | 3-pyridyl | iPr | Solid |
| 48 | Me | OH | Me | (Ia') | 3-(2,6-dimethyl-pyridyl) | Et | Solid |
| 49 | Me | OH | Me | (Ia') | 3-(2,6-dimethyl-pyridyl) | iPr | 131–133 |
| 50 | Me | OH | Me | (Ia') | 5-(2-methyl-pyridyl) | Et | Solid |
| 51 | Me | OH | Me | (Ia') | 5-(2-methyl-pyridyl) | iPr | Solid |
| 52 | Me | OH | Me | (Ib') (E) | 3-(2,6-dimethyl-pyridyl) | iPr | 122–124 |
| 53 | OMe | OH | Me | (Ia') | 2-pyrimidinyl | Et | 133–136 |
| 54 | OEt | OH | Me | (Ib') (E) | 3-pyridyl | Et | Solid |

TABLE 1-continued (Ia')

$$X^2\text{-}C_6H_2(X^3)(X^4)\text{-}CH(PO_3R^1R^2)\text{-}CH_2\text{-}NH\text{-}Het$$

(Ib')

$$X^2\text{-}C_6H_2(X^3)(X^4)\text{-}C(PO_3R^1R^2)\text{=}CH\text{-}NH\text{-}Het$$

| Cpd | $X^2$ | $X^3$ | $X^4$ | Formula (isomer) | Het | $R^1, R^2$ | mp (° C.) |
|---|---|---|---|---|---|---|---|
| 55 | OEt | OH | Me | (Ia') | 3-pyridyl | Et | 155–156 |
| 56 | OEt | OH | Me | (Ib') (E) | 3-(2,6-dimethyl-pyridyl) | Et | Solid |
| 57 | OEt | OH | Me | (Ia') | 3-(2,6-dimethyl-pyridyl) | Et | Solid |
| 58 | OEt | OH | Me | (Ib') (E) | 3-(2,6-dimethyl-pyridyl) | iPr | Solid |
| 59 | OEt | OH | Me | (Ia') | 3-(2,6-dimethyl-pyridyl) | iPr | Solid |
| 60 | OMe | OH | Me | (Ia') | 2-(4,6-dimethyl-pyridyl) | Et | Solid |
| 61 | OMe | OH | Me | (Ia') | 2-(4,6-dimethyl-pyrimidinyl) | Et | Solid |
| 62 | OMe | OH | Me | (Ia') | 2-(4-OMe-6-Me-pyrimidinyl) | Et | 160–164 |
| 63 | OMe | OH | Me | (Ib') (E) | 5-pyrimidinyl | Et | Solid |
| 64 | OMe | OH | Me | (Ia') | 5-pyrimidinyl | Et | wax |
| 65 | OMe | OH | Me | (Ia') | 5-(2-methyl-pyrimidinyl) | Et | Solid |
| 66 | OMe | OH | Me | (Ib') (Z) | 5-(4-methyl-pyrimidinyl) | Et | Solid |
| 67 | OMe | OH | Me | (Ib') (E) | 5-(4-methyl-pyrimidinyl) | Et | Solid |
| 68 | OMe | OH | Me | (Ia') | 5-(4-methyl-pyrimidinyl) | Et | Solid |
| 69 | OMe | OH | Me | (Ib') (Z) | 5-(2,6-dimethyl-pyrimidinyl) | Et | Solid |
| 70 | OMe | OH | Me | (Ib') (E) | 5-(2,6-dimethyl-pyrimidinyl) | Et | Solid |
| 71 | OMe | OH | Me | (Ia') | 5-(2,6-dimethyl-pyrimidinyl) | Et | 172–174 |
| 72 | OMe | OH | Me | (Ia') | 2-thiazolyl | Et | 85–87 |
| 73 | OMe | OH | Me | (Ia') | 2-(5-methyl-thiazolyl) | Et | 178–180 |
| 74 | OMe | OH | Me | (Ia') | 2-(5-methyl-thiazolyl) | Et | Solid |
| 75 | OMe | OH | Me | (Ia') | 2-(1,3,4-thia-diazolyl) | Et | Solid |
| 76 | OMe | OH | Me | (Ib') (E) | 2-(5-methyl-pyrizinyl) | Et | Solid |
| 77 | OMe | OH | Me | (Ia') | 2-(5-methyl-pyrizinyl) | Et | 118–121 |
| 78 | OMe | OH | Me | (Ia') | 3-(6-methyl-pyridazinyl) | Et | Solid |
| 79 | OMe | OH | Me | (Ib') (E) | 4-(1,3,5-tri-methylpyrazolyl) | Et | Solid |
| 80 | OMe | OH | Me | (Ia') | 4-(1,3,5-tri-methylpyrazolyl) | Et | wax |
| 81 | OMe | OH | Me | (Ia') | 2-(benzothiazolyl) | Et | Solid |
| 82 | OMe | OH | H | (Ia') | 3-(2,6-dimethyl-pyridyl) | Et | Solid |
| 83 | OH | OMe | H | (Ia') | 3-(2,6-dimethyl-pyridyl) | Et | Solid |
| 84 | OMe | OH | Me | (Ia') | 3-pyridyl | Me | Solid |
| 85 | OMe | OH | Me | (Ia') | 3-(2,6-dimethyl-pyridyl) | Me | Solid |
| 86 | OMe | OH | Me | (Ia') | 3-(2,6-dimethyl-pyrazolyl) | Et | Solid |
| 87 | OMe | OH | Me | (Ia') | 3-isoxazolyl | Et | Solid |
| 88 | OMe | OH | Me | (Ia') | 3-(5-methyl-isozazolyl) | Et | Solid |
| 89 | OMe | OH | Me | (Ia') | 5-(3-methyl-isoxazolyl) | Et | Solid |
| 90 | OMe | OH | Me | (Ia') | 2-(4-methyl-oxazolyl) | Et | Solid |
| 91 | OMe | OH | Me | (Ia') | 2-(4-methyl-oxazolyl) | Et | Solid |
| 92 | H | H | H | (Ia') | 3-(2,6-dimethyl-pyridyl) | Et | Solid |
| 93 | H | Cl | H | (Ia') | 3-(2,6-dimethyl-pyridyl) | Et | oil |
| 94 | H | Me | H | (Ia') | 3-(2,6-dimethyl-pyridyl) | Et | Solid |
| 95 | H | MeO | H | (Ia') | 3-(2,6-dimethyl-pyridyl) | Et | oil |

Summarized in TABLE 2 are aminophosphonates of formula (Ia) where $Z^0$ is Me, $X^1$ and $X^5$ are H, and n=0, designated as (Ia"), prepared according to the processes hereinbefore described:

TABLE 2

(Ia")

$$X^2\text{-}C_6H_2(X^3)(X^4)\text{-}CH(PO_3R^1R^2)\text{-}CH(Me)\text{-}NH\text{-}Het$$

| Cpd | $X^2$ | $X^3$ | $X^4$ | Formula | Het | $R^1, R^2$ | mp (° C.) |
|---|---|---|---|---|---|---|---|
| 96 | OMe | OH | Me | (Ia") | 3-picoyl | Et | Solid |
| 97 | OMe | OH | Me | (Ia") | 2-pyridyl | Et | Oil |
| 98 | OMe | OH | Me | (Ia") | 2-(2-ethylpyridyl) | Et | Oil |

Example 30

Biological Data

A. Lp(a) Lowering Activity

1. In vitro Data

The compounds of formula (I) were assayed for being able to effectively lower the production of apo (a) in primary cultures of Cynomolgus hepatocytes.

Protocol

Hepatocytes were isolated from livers of male adult Cynomolgus monkeys by the two-step collagenase perfusion method according to C. Guguen-Guillouzo and A. Guillouzo "Methods for preparation of adult and fetal hepatocytes" p.1–12 in "Isolated and Cultured Hepatocytes", les editions Inserm Paris and John Libbey Eurotext London (1986).

The viability of cells was determined by Trypan blue staining. The cells were then seeded at a density of 1.5–2.105 viable cells per 2 cm$^2$ in 24 well tissue culture plates in a volume of 500 µl per well of Williams E tissue culture medium containing 10% fetal calf serum. Cells were incubated for 6–24 hours at 37° C. in a $CO_2$ incubator (5% $CO_2$) in the presence of 20 µM of the test compounds dissolved in ethanol. Four wells were used for each compound. Nicotinic acid and steroid hormones were used as references to validate the assay system since they are known to decrease apo (a) in man. Control cells were incubated in the presence of ethanol only.

The amount of apo (a) secreted in culture medium was assayed directly by ELISA using a commercially available kit. Changes in apo (a) concentration in culture medium are given as the percentage of value measured for the control plates.

Results

The compounds No. 1, 5, 6, 7, 13, 14, 15, 17, 18, 19, 20, 22, 33, 35, 36, 37, 38, 39, 40, 42, 43, 44, 47, 48, 49, 50, 51, 53, 55, 57, 59, 61, 62, 68, 71, 73, 77, 81, 82, 83, 85, 86, 87, 88, 89, 92, 93, 94 and the compounds of examples 24, 25, 26 and 27 were tested at 20 µM and were found to lower the apo (a) secretion in the range between −19 to −55%.

2. In Vivo Data

Study Protocol

Male cynomolgus monkeys weighing between 3 and 7 kg were divided into groups of 3 to 4 animals each. Prior to treatment their plasma Lp(a) levels were followed over a two month period to ascertain a constant baseline value. Test compounds were given orally by gavage at the dose of 50 mg/kg/day for 2 weeks and Lp(a) was measured at days 7 and 14. At the end of the dosing period, animals were maintained for a treatment free period of 4 weeks, whereupon the decreased plasma Lp(a) levels returned to pretreatment levels. This control provided proof that the decrease in Lp(a) measured was caused by the pharmacological activity of the test compounds. At Days −1 and 7 or 14, after an overnight fast blood samples were collected on EDTA and Lp(a) was measured by the highly sensitive and specific ELISA test. Results (mean of 3–4 values of each group) were expressed as % of pre-dose (Day −1).

Results

Selected compounds of formula (I) were tested under the experimental conditions to investigate their pharmacological activity in vivo. The compounds No 15, 18, 33, 36, 38, 39, 40 and 44 lower plasma Lp(a) in the range of −20% to −40% (values measured at Day 7 or 14,% changes from pre-dose at Day −1).

In a further study, the compounds of Example 11 were tested at a dose of 12.5 and 25 mg/kg/day. These compounds were found to lower plasma Lp(a) in the range of −5% to −15% at the 12.5 mg dose and in the range from −20 to −25% at the 25 mg/kg dose (values measured at Day 7 or 14,% changes from pre-dose at Day −1).

B. Cholesterol Lowering Activity

Study Protocol.

Male cynomolgus monkeys weighing between 3 and 7 kg were divided into groups of 3 to 4 animals each. Prior to treatment, their plasma cholesterol, LDL cholesterol and apo B levels were followed over a one month period to ascertain a constant baseline value. Test compounds were given orally by gavage at the dose of 50 mg/kg/day for 2 weeks and apo B, LDL cholesterol, and total plasma cholesterol were measured at days 7 and 14. At the end of the dosing period, animals were maintained for a treatment-free period of 4 weeks, whereupon their cholesterol levels returned to pre-treatment levels. This control provided proof that the decrease in cholesterol measured was caused by the pharmacological activity of the test compounds. At Days −1 and 7 or 14, after an overnight fast, blood samples were collected on EDTA and apo B was measured by an ELISA method (Morwell diagnostics), LDL cholesterol by an immuno turbidimetric method (Boehringer) and total plasma cholesterol by an enzymatic method (CHOD-PAP, Boehringer). Results (mean of 3–4 values of each group) were expressed as % of pre-dose (Day −1).

Results

Selected compounds of formula (I) were tested under the experimental conditions described to investigate their pharmacological activity in vivo. The compounds No 15, 18, 38, 36, 39, 40 and 44 lower apo B in the range from −28% to −42%, LDL cholesterol in the range from −14% to −22% and total plasma cholesterol from −17% to −20% (values measured at Day 7 or Day 14,% changes from pre-dose at Day −1).

What is claimed is:

1. A compound of formula (Ia):

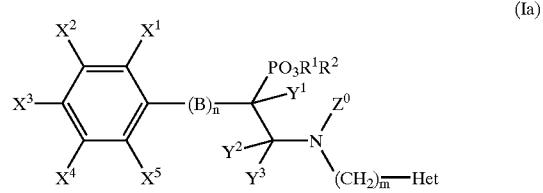

or a compound of formula (Ib):

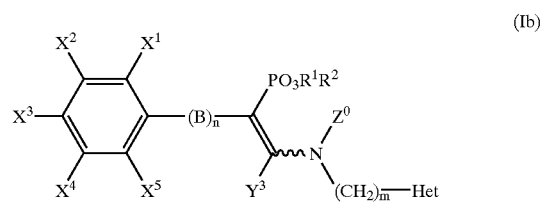

in which:

$X^1$, $X^2$, $X^3$, $X^4$ and $X^5$ are independently hydrogen, hydroxy, hydroxymethyl, $C_1$–$C_3$ alkoxymethyl straight or branched $C_1$–$C_8$ alkyl, straight or branched $C_1$–$C_8$ alkoxy, $C_3$–$C_6$ cycloalkyl, $C_3$–$C_6$ cycloalkoxy, norbornyl, adamantyl, amino, primary or secondary amino substituted with $C_1$–$C_3$ alkyl, cyano, halogen (F, Cl, Br, I), and nitro; or $X^2$ may be combined with $X^3$, or $X^4$ may be combined with $X^5$, to form a 5- to 6-membered alkylidenedioxy ring optionally substituted with a $C_1$–$C_4$ alkyl group; or $X^4$ may be combined with $X^5$ to form a 5- to 6-membered alkylidene ring optionally substituted with a $C_1$–$C_4$ alkyl group, with the proviso that for formula (Ia) $X^1$ is hydrogen, or methyl, $X^2$ is methoxy, ethoxy, methyl or hydroxy, $X^3$ is hydrogen, hydroxy, methoxy, ethyl, ethyl or hydroxymethyl, $X^4$ is hydrogen, methoxy or methyl and $X^5$ is hydrogen;

$R^1$ and $R^2$, are independently hydrogen or a straight or branched $C_1$–$C_6$ alkyl;

B is $CH_2$ or $CH_2$—$CH_2$;

n is zero or 1;

$Z^o$ is H, straight or branched $C_1$–$C_4$ alkyl, $C_1$–$C_4$ alkylcarbonyl, or $C_1$–$C_4$ perfluoroalkylcarbonyl;

m is zero or an integer from 1 to 4;

Het is an optionally substituted heteroaryl group selected from the group consisting of pyridyl, pyrimidyl, pyrazinyl, pyridazinyl, thiazolyl, thiadiazolyl, benzothiazolyl, isoxazolyl, pyrazolyl, triazinyl, and imidazolyl;

for a compound of formula (Ia), $Y^1$, $Y^2$ and $Y^3$ are independently hydrogen or $C_1$–$C_4$ alkyl and for a compound of formula (Ib), $Y^3$ is hydrogen or $C_1$–$C_4$ alkyl;

or a pharmaceutically acceptable salt thereof.

2. The compound of claim 1, wherein said compound is a compound of formula (Ia).

3. The compound of claim 1, wherein said compound is a compound of formula (Ib).

4. The compound of claim 3, wherein said compound of formula (Ib) is the Z-isomer, the E-isomer, or a mixture thereof.

5. The compound of claim 1, wherein $X^2$ is methoxy, is hydroxy and $X^4$ is methyl.

6. The compound of claim 1, wherein n is zero.

7. The compound of claim 1, wherein $R^1$ and $R^2$ are independently $C_1$–$C_3$ alkyl.

8. The compound of claim 7, wherein $R^1$ and $R^2$ are independently ethyl or isopropyl.

9. The compound of claim 1, wherein said optionally substituted hetroaryl group selected from the group consisting of pyridyl, pyrimidyl, pyrazinyl, pyridazinyl, thiazolyl, thiadiazolyl, benzothiazolyl, isoxazolyl, pyrazolyl, triazinyl, and imidazolyl is substituted with one or two methyl groups.

10. The compound of claim 1, wherein Het is 2,6-dimethylpyridyl or pyrazinyl.

11. A compound selected from the group consisting of:

(Z)-diethyl α-(3,5-dimethoxy-4-hydroxyphenyl)-β-[N-(3-pyridyl)-amino]-vinylphosphonate;

(Z)-diethyl α-(4-hydroxy-3-methoxy-5-methylphenyl)-β-[N-(3-pyridyl)-amino]-vinylphosphonate;

(Z)-diisopropyl α-(4-hydroxy-3-methoxy-5-methylphenyl)-β-[N-(3-pyridyl)-amino]-vinylphosphonate;

(E)-diethyl α-(3,5-dimethoxy-4-hydroxyphenyl)-β-[N-(3-pyridyl)-amino]-vinylphosphonate;

(E)-diisopropyl α-(3,5-dimethoxy-4-hydroxyphenyl)-β-[N-(3-pyridyl)-amino]-vinylphosphonate;

(E)-diethyl α-(4-hydroxy-3-methoxy-5-methylphenyl)-β-[N-(3-pyridyl)-amino]-vinylphosphonate;

(E)-diisopropyl α-(4-hydroxy-3-methoxy-5-methylphenyl)-β-[N-(3-pyridyl)-amino]-vinylphosphonate;

(Z)-diethyl α-(3,5-dimethoxy-4-hydroxyphenyl)-β-[N-(3-(2,6-dimethyl)pyridyl))-amino]-vinylphosphonate;

(Z)-diethyl α-(4-hydroxy-3-methoxy-5-methylphenyl)-β-[N-(3-(2,6-dimethyl)pyridyl))-amino]-vinylphosphonate;

(E)-diisopropyl α-(3,5-dimethoxy-4-hydroxyphenyl)-β-[N-(3-(2,6-dimethyl)pyridyl))-amino]-vinylphosphonate;

(E)-diethyl α-(4-hydroxy-3-methoxy-5-methylphenyl)-β-[N-(3-(2,6-dimethyl)pyridyl))-amino]-vinylphosphonate;

(E)-diisopropyl α-(4-hydroxy-3-methoxy-5-methylphenyl)-β-[N-(3-(2,6-dimethyl)pyridyl))-amino]-vinylphosphonate;

(E)-diethyl α-(4-hydroxy-3-methoxy-5-methylphenyl)-β-[N-(5-(2-methyl)pyridyl))-amino]-vinylphosphonate;

(E)-diethyl α-(4-hydroxy-3-methoxy-5-methylphenyl)-β-[N-(5-(2-methoxy)pyridyl))-amino]-vinylphosphonate;

(Z)-diethyl α-(3,5-dimethoxy-4-hydroxyphenyl)-β-[N-(pyrazinyl)-amino]-vinylphosphonate;

(Z)-diisopropyl β-(3,5-dimethoxy-4-hydroxyphenyl)-β-[N-(pyrazinyl)-amino]-vinylphosphonate;

(Z)-diethyl α-(4-hydroxy-3-methoxy-5-methylphenyl)-β-[N-(pyrazinyl)-amino]-vinylphosphonate;

(E)-diisopropyl α-(3,5-dimethoxy-4-hydroxyphenyl)-β-[N-(pyrazinyl)-amino]-vinylphosphonate;

(E)-diethyl α-(4-hydroxy-3-methoxy-5-methylphenyl)-β-[N-(pyrazinyl)-amino]-vinylphosphonate;

(Z)-diethyl α-(3,5-dimethoxy-4-hydroxyphenyl)-β-[N-(2-pyrimidinyl)-amino]-vinylphosphonate;

(Z)-diisopropyl α-(3,5-dimethoxy-4-hydroxyphenyl)-B-[N-(2-pyrimidinyl)-amino]-vinylphosphonate;

(E)-diethyl α-(3,5-dimethoxy-4-hydroxyphenyl)-β-[N-(2-pyrimidinyl)-amino]-vinylphosphonate;

(E)-diisopropyl α-(3,5-dimethoxy-4-hydroxyphenyl)-β-[N-(2-pyrimidinyl-amino)-vinylphosphonate;

(Z)-diethyl α-(4-hydroxy-3-methoxy-5-methylphenyl)-β-[N-(2-pyrimidinyl)-amino]-vinylphosphonate;

(Z)-diisopropyl α-(3,5-dimethyl-4-hydroxyphenyl)-β-[N-(3-(2,6-dimethylpyridyl))-amino]-vinylphosphonate;

(E)-diethyl α-(4-hydroxy-3-methoxy-5-methylphenyl)-β-[N-(2-pyrimidinyl)-amino]-vinylphosphonate;

(E)-diethyl α-(3,5-dimethyl-4-hydroxyphenyl)-β-[N-(3-pyridyl)-amino]-vinylphosphonate;

(E)-diisopropyl α-(3,5-dimethyl-4-hydroxyphenyl)-β-[N-(3-pyridyl)-amino]-vinylphosphonate;

(E)-diethyl α-(3,5-dimethyl-4-hydroxyphenyl)-β-[N-(3-(2,6-dimethylpyridyl))-amino]-vinylphosphonate;

(E)-diethyl α-(3,5-dimethyl-4-hydroxyphenyl)-β-[N-(5-(2-methylpyridyl))amino]-vinylphosphonate;

(E)-diisopropyl α-(3,5-dimethyl-4-hydroxyphenyl)-β-[N-(5-(2-methylpyridyl))-amino]-vinylphosphonate;

(E)-diisopropyl α-(3,5-dimethyl-4-hydroxyphenyl)-β-[N-(3-(2,6-dimethylpyridyl))-amino]-vinylphosphonate;

(E)-diethyl α-(3-ethoxy-4-hydroxy-5-methylphenyl)-β-[N-(3-pyridyl)-amino]-vinylphosphonate;

(E)-diethyl α-(3-ethoxy-4-hydroxy-5-methylphenyl)-β-[N-(3-(2,6-dimethylpyridyl))-amino]-vinylphosphonate;

(E)-diisopropyl α-(3-ethoxy-4-hydroxy-5-methylphenyl)-β-[N-(3-(2,6-dimethylpyridyl))-amino]-vinylphosphonate;

(E)-diethyl α-(4-hydroxy-3-methoxy-5-methylphenyl)-β-[N-(5-pyrimidinyl)-amino]-vinylphosphonate;

(Z)-diethyl α-(4-hydroxy-3-methoxy-5-methylphenyl)-β-[N-(5-(4-methylpyrimidinyl))-amino]-vinylphosphonate;

(E)-diethyl α-(4-hydroxy-3-methoxy-5-methylphenyl)-β-[N-(5-(4-methylpyrimidinyl))-amino]-vinylphosphonate;

(Z)-diethyl α-(4-hydroxy-3-methoxy-5-methylphenyl)-β-[N-(5-(2,6-dimethylpyrimidinyl))-amino]-vinylphosphonate;

(E)-diethyl α-(4-hydroxy-3-methoxy-5-methylphenyl)-β-[N-(5-(2,6-dimethylpyrimidinyl))-amino]-vinylphosphonate;

(E)-diethyl α-(4-hydroxy-3-methoxy-5-methylphenyl)-β-[N-(2-(5-methylpyrazinyl))-amino]-vinylphosphonate;

(E)-diethyl α-(4-hydroxy-3-methoxy-5-methylphenyl)-β-[N-(4-(1,3,5-trimethylpyrazolyl))-amino]-vinylphosphonate;

diethyl α-(3-hydroxy-4-methoxyphenyl)-β-[N-(3-(2,6-dimethyl)pyridyl))-amino]-ethylphosphonate;

diethyl α-phenyl-β-[N-(3-(2,6-dimethylpyridyl))-amino]-ethylphosphonate;

diethyl α-(4-methylphenyl)-β-[N-(3-(2,6-dimethylpyridyl))-amino]-ethylphosphonate;

diethyl α-(4-methoxyphenyl)-β-[N-(3-(2,6-dimethylpyridyl))-amino]-ethylphosphonate, or a pharmaceutically acceptable salt thereof.

12. A compound selected from selected from the group consisting of:

(±)-diethyl α-(3,5-dimethoxy-4-hydroxyphenyl)-β-[N-(pyrazinyl)-amino]-ethylphosphonate;

(±)-diethyl α-(4-hydroxy-3-methoxy-5-methylphenyl)-β-[N-(pyrazinyl)-amino]-ethylphosphonate;

(±)-diisopropyl α-(4-hydroxy-3-methoxy-5-methylphenyl)-β-[N-3-(2,6-dimethyl)pyridyl-amino]-ethylphosphonate;

(±)-diethyl α-(4-hydroxy-3-methoxy-5-methylphenyl)-β-[N-(3-(2,6-dimethylpyridyl))-amino]-ethylphosphonate;

(+)-diethyl α-(4-hydroxy-3-methoxy-5-methylphenyl)-β-[N-(3-(2,6-dimethylpyridyl))-amino]-ethylphosphonate and the dihydrogen phosphate salt thereof (−)-diethyl α-(4-hydroxy-3-methoxy-5-methylphenyl)-β-[N-(3-(2,6-dimethylpyridyl))-amino]-ethylphosphonate and the dihydrogen phosphate salt thereof, or a pharmaceutically acceptable salt thereof.

13. A pharmaceutical composition comprising a compound as claimed in claim 1 and a pharmaceutically acceptable excipient.

14. A method for decreasing plasma levels of apo (a), lipoprotein (a), apo B, LDL cholesterol and total cholesterol comprising administering to a subject an effective amount of a compound of formula (Ia):

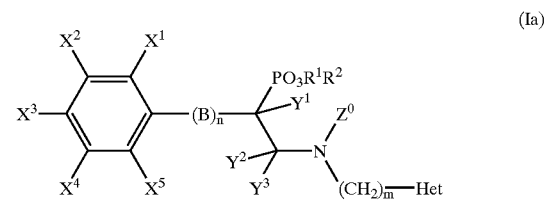

(Ia)

or a compound of formula (Ib):

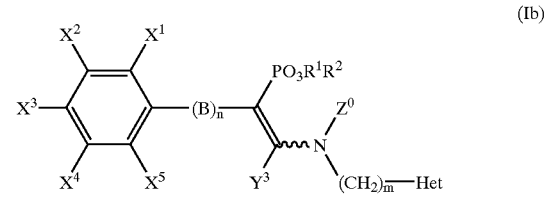

(Ib)

in which:

$X^1$, $X^2$, $X^3$, $X^4$ and $X^5$ are independently hydrogen, hydroxy, hydroxymethyl, $C_1$–$C_3$ alkoxymethyl straight or branched $C_1$–$C_8$ alkyl, straight or branched $C_1$–$C_8$ alkoxy, $C_3$–$C_6$ cycloalkyl, $C_3$–$C_6$ cycloalkoxy, norbornyl, adamantyl, amino, primary or secondary amino substituted with $C_1$–$C_3$ alkyl, cyano, halogen (F, Cl, Br, I), and nitro; or $X^2$ may be combined with $X^3$, or $X^4$ may be combined with $X^5$, to form a 5- to 6-membered alkylidenedioxy ring optionally substituted with a $C_1$–$C_4$ alkyl group; or $X^4$ may be combined with $X^5$ to form a 5- to 6-membered alkylidene ring optionally substituted with a $C_1$–$C_4$ alkyl group, with the proviso that for formula (Ia) $X^1$ is hydrogen, or methyl, $X^2$ is methoxy, ethoxy, methyl or hydroxy, $X^3$ is hydrogen, hydroxy, methoxy, ethyl, ethyl or hydroxymethyl, $X^4$ is hydrogen, methoxy or methyl and $X^5$ is hydrogen;

$R^1$ and $R^2$, are independently hydrogen or a straight or branched $C_1$–$C_6$ alkyl;

B is $CH_2$ or $CH_2$—$CH_2$;

n is zero or 1;

$Z^0$ is H, straight or branched $C_1$–$C_4$ alkyl, $C_1$–$C_4$ alkylcarbonyl, or $C_1$–$C_4$ perfluoroalkylcarbonyl;

m is zero or an integer from 1 to 4;

Het is an optionally substituted heteroaryl group selected from the group consisting of pyridyl, pyrimidyl, pyrazinyl, pyridazinyl, thiazolyl, thiadiazolyl, benzothiazolyl, isoxazolyl, pryazolyl, triazinyl, and imidazolyl; and for a compound of formula (Ia), $Y^1$, $Y^2$ and $Y^3$ are independently hydrogen or $C_1$–$C_4$ alkyl and for a compound of formula (Ib), $Y^3$ is hydrogen or $C_1$–$C_4$ alkyl; or a pharmaceutically acceptable salt thereof.

15. A method for treatment of thrombosis secondary to elevated plasma levels of apo (a), lipoprotein (a), apo B, LDL cholesterol, and/or total cholesterol, comprising administering to a patient in need of such treatment an effective amount to a compound of formula (Ia):

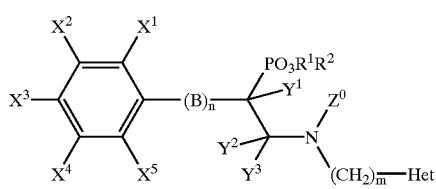

(Ia)

or a compound of formula (Ib):

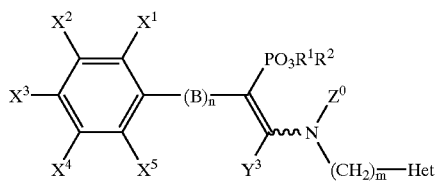

(Ib)

in which:

$X^1$, $X^2$, $X^3$, $X^4$ and $X^5$ are independently hydrogen, hydroxy, hydroxymethyl, $C_1$–$C_3$ alkoxymethyl straight or branched $C_1$–$C_8$ alkyl, straight or branched $C_1$–$C_8$ alkoxy, $C_3$–$C_6$ cycloalkyl, $C_3$–$C_6$ cycloalkoxy, norbornyl, adamantyl, amino, primary or secondary amino substituted with $C_1$–$C_3$ alkyl, cyano, halogen (F, Cl, Br, I), and nitro; or $X^2$ may be combined with $X^3$, or $X^4$ may be combined with $X^5$, to form a 5- to 6-membered alkylidenedioxy ring optionally substituted with a $C_1$–$C_4$ alkyl group; or $X^4$ may be combined with $X^5$ to form a 5- to 6-membered alkylidene ring optionally substituted with a $C_1$–$C_4$ alkyl group, with the proviso that for formula (Ia) $X^1$ is hydrogen, or methyl, $X^2$ is methoxy, ethoxy, methyl or hydroxy, $X^3$ is hydrogen, hydroxy, methoxy, ethyl, ethyl or hydroxymethyl, $X^4$ is hydrogen, methoxy or methyl and $X^5$ is hydrogen;

$R^1$ and $R^2$, are independently hydrogen or a straight or branched $C_1$–$C_6$ alkyl;

B is $CH_2$ or $CH_2$—$CH_2$;

n is zero or 1;

$Z^0$ is H, straight or branched $C_1$–$C_4$ alkyl, $C_1$–$C_4$ alkylcarbonyl, or $C_1$–$C_4$ perfluoroalkylcarbonyl;

m is zero or an integer from 1 to 4;

Het is an optionally substituted heteroaryl group selected from the group consisting of pyridyl, pyrimidyl, pyrazinyl, pyridazinyl, thiazolyl, thiadiazolyl, benzothiazolyl, isoxazolyl, pryazolyl, triazinyl, and imidazolyl; and for a compound of formula (Ia), $Y^1$, $Y^2$ and $Y^3$ are independently hydrogen or $C_1$–$C_4$ alkyl and for a compound of formula (Ib), $Y^3$ is hydrogen or $C_1$–$C_4$ alkyl; or a pharmaceutically acceptable salt thereof.

16. A method for the treatment of restenosis following angioplasty comprising administering to a patient in need of such treatment an effective amount of a compound of formula (Ia):

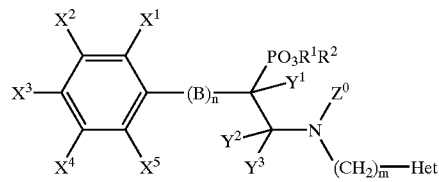

(Ia)

or a compound of formula (Ib):

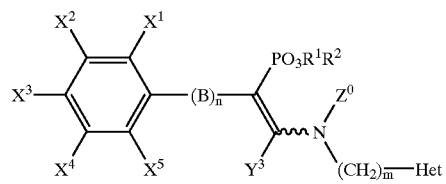

(Ib)

in which:

$X^1$, $X^2$, $X^3$, $X^4$ and $X^5$ are independently hydrogen, hydroxy, hydroxymethyl, $C_1$–$C_3$ alkoxymethyl straight or branched $C_1$–$C_8$ alkyl, straight or branched $C_1$–$C_8$ alkoxy, $C_3$–$C_6$ cycloalkyl, $C_3$–$C_6$ cycloalkoxy, norbornyl, adamantyl, amino, primary secondary amino substituted with $C_1$–$C_3$ alkyl, cyano, halogen (F, Cl, Br, I), and nitro; or $X^2$ may be combined with $X^3$, or $X^4$ may be combined with $X^5$, to form a 5- to 6-membered alkylidenedioxy ring optionally substituted with a $C_1$–$C_4$ alkyl group; or $X^4$ may be combined with $X^5$ to form a 5- to 6-membered alkylidene ring optionally substituted with a $C_1$–$C_4$ alkyl group, with the proviso that for formula (Ia) $X^1$ is hydrogen, or methyl, $X^2$ is methoxy, ethoxy, methyl or hydroxy, $X^3$ is hydrogen, hydroxy, methoxy, ethyl, ethyl or hydroxymethyl, $X^4$ is hydrogen, methoxy or methyl and $X^5$ is hydrogen;

$R^1$ and $R^2$, are independently hydrogen or a straight or branched $C_1$–$C_6$ alkyl;

B is $CH_2$ or $CH_2$—$CH_2$;

n is zero or 1;

$Z^0$ is H, straight or branched $C_1$–$C_4$ alkyl, $C_1$–$C_4$ alkylcarbonyl, or $C_1$–$C_4$ perfluoroalkylcarbonyl;

m is zero or an integer from 1 to 4;

Het is an optionally substituted heteroaryl group selected from the group consisting of pyridyl, pyrimidyl, pyrazinyl, pyridazinyl, thiazolyl, thiadiazolyl, benzothiazolyl, isoxazolyl, pryazolyl, triazinyl, and imidazolyl; and for a compound of formula (Ia), $Y^1$, $Y^2$ and $Y^3$ are independently hydrogen or $C_1$–$C_4$ alkyl and for a compound of formula (Ib), $Y^3$ is hydrogen or $C_1$–$C_4$ alkyl; or a pharmaceutically acceptable salt thereof.

17. A method for the prevention and/or treatment of atherosclerosis secondary to elevated plasma levels of apo (a), lipoprotein (a), apo B, LDL cholesterol, and/or total cholesterol, comprising administering to a patient in need of such treatment effective amount of a compound of formula (Ia):

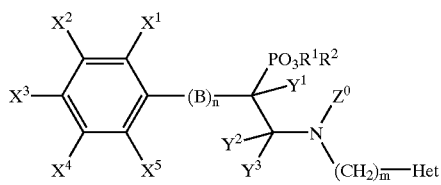
(Ia)

or a compound of formula (Ib):

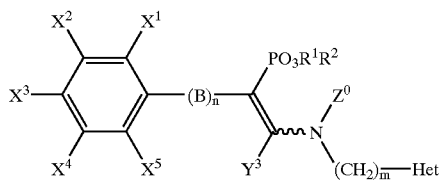
(Ib)

in which:

$X^1$, $X^2$, $X^3$, $X^4$ and $X^5$ are independently hydrogen, hydroxy, hydroxymethyl, $C_1$–$C_3$ alkoxymethyl straight or branched $C_1$–$C_8$ alkyl, straight or branched $C_1$–$C_8$ alkoxy, $C_3$–$C_6$ cycloalkyl, $C_3$–$C_6$ cycloalkoxy, norbornyl, adamantyl, amino, primary or secondary amino substituted with $C_1$–$C_3$ alkyl, cyano, halogen (F, Cl, Br, I), and nitro; or $X^2$ may be combined with $X^3$, or $X^4$ may be combined with $X^5$, to form a 5- to 6-membered alkylidenedioxy ring optionally substituted with a $C_1$–$C_4$ alkyl group; or $X^4$ be combined with $X^5$ to form a 5- to 6-membered alkylidene ring optionally substituted with a $C^1$–$C_4$ alkyl group, with the proviso that for formula (Ia) $X^1$ is hydrogen, or methyl, $X^2$ is methoxy, ethoxy, methyl or hydroxy, $X^3$ is hydrogen, hydroxy, methoxy, ethyl, ethyl or hydroxymethyl, $X^4$ is hydrogen, methoxy or methyl and $X^5$ is hydrogen;

$R^1$ and $R^2$, are independently hydrogen or a straight or branched $C_1$–$C_6$ alkyl;

B is $CH_2$ or $CH_2$—$CH_2$;

n is zero or 1;

$Z^0$ is H, straight or branched $C_1$–$C_4$ alkyl, $C_1$–$C_4$ alkylcarbonyl, or $C_1$–$C_4$ perfluoroalkylcarbonyl;

m is zero or an integer from 1 to 4;

Het is an optionally substituted heteroaryl group selected from the group consisting of pyridyl, pyrimidyl, pyrazinyl, pyridazinyl, thiazolyl, thiadiazolyl, benzothiazolyl, isoxazolyl, pryazolyl, triazinyl, and imidazolyl; and for a compound of formula (Ia), $Y^1$, $Y^2$ and $Y^3$ are independently hydrogen or $C_1$–$C_4$ alkyl and for a compound of formula (Ib), $Y^3$ is hydrogen or $C_1$–$C_4$ alkyl; or a pharmaceutically acceptable salt thereof.

18. The method of claim 17, wherein said patient is resistant to treatment with statins.

* * * * *

UNITED STATES PATENT AND TRADEMARK OFFICE
CERTIFICATE OF CORRECTION

PATENT NO. : 6,706,698 B2
DATED : March 16, 2004
INVENTOR(S) : Hieu Trung Phan et al.

It is certified that error appears in the above-identified patent and that said Letters Patent is hereby corrected as shown below:

Column 45,
Line 10, please delete "ethyl" and insert -- methyl -- therefor.
Line 39, please insert -- $X^3$ -- after "methoxy," therefor.

Column 46,
Line 27, please delete "(Z)-diisopropyl β-(3,5-dimethoxy-4-hydroxyphenyl)-β-" and insert -- (Z)-diisopropyl α-(3,5-dimethoxy-4-hydroxyphenyl)-ß- -- therefor.
Line 37, please delete "(Z)-diisopropyl α-(3,5-dimethoxy-4-hydroxyphenyl)-B-" and insert -- (Z)-diisopropyl α-(3,5-dimethoxy-4-hydroxyphenyl)-ß- -- therefor.

Column 47,
Line 54, please insert -- ; -- after "thereof" therefor.
Line 38, please delete 'selected from' after compound therefor.

Column 48,
Line 41, please delete "ethyl" and insert -- methyl -- therefor.

Column 49,
Line 42, please delete "ethyl" and insert -- methyl -- therefor.

Column 50,
Line 40, please delete "ethyl" and insert -- methyl -- therefor.
Line 66, after "treatment" please insert -- an -- therefor.

Signed and Sealed this

Twenty-seventh Day of July, 2004

JON W. DUDAS
*Acting Director of the United States Patent and Trademark Office*